(12) United States Patent
Morris

(10) Patent No.: US 6,960,476 B2
(45) Date of Patent: Nov. 1, 2005

(54) METHOD AND APPARATUS FOR ANALYZING MIXTURES OF GASES

(75) Inventor: Patricia A. Morris, Montchanin, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 523 days.

(21) Appl. No.: 09/977,791

(22) Filed: Oct. 15, 2001

(65) Prior Publication Data

US 2002/0121440 A1 Sep. 5, 2002

Related U.S. Application Data

(60) Provisional application No. 60/240,619, filed on Oct. 16, 2000, and provisional application No. 60/246,946, filed on Nov. 9, 2000.

(51) Int. Cl.[7] ............... G01N 7/00; G01N 21/00; G01N 27/00; G01N 31/00; G01N 33/00

(52) U.S. Cl. ............... 436/149; 436/43; 436/151; 422/50; 422/83; 422/88; 422/94; 422/95; 422/96; 422/97; 422/98; 73/1.01; 73/1.02; 73/23.2; 73/23.31; 73/31.06

(58) Field of Search ............... 422/50, 83, 88, 422/94, 95, 96, 97, 98; 436/43, 149, 151; 73/1.01, 1.02, 23.2, 23.31, 31.06

(56) References Cited

U.S. PATENT DOCUMENTS

| | | | |
|---|---|---|---|
| 4,007,435 A | 2/1977 | Tien | |
| 4,151,503 A | 4/1979 | Cermak et al. | |
| 4,225,842 A | 9/1980 | Schleselman et al. | |
| 4,234,542 A | 11/1980 | Romine | |
| 4,387,359 A | 6/1983 | Tien et al. | |
| 4,457,161 A | 7/1984 | Iwanaga et al. | |
| 4,535,316 A | 8/1985 | Wertheimer et al. | |
| 4,542,640 A | 9/1985 | Clifford | |
| 4,770,760 A | 9/1988 | Noda et al. | |
| 5,239,483 A | 8/1993 | Weir | |
| 5,426,934 A | 6/1995 | Hunt et al. | |
| 5,554,273 A | 9/1996 | Demmin et al. | |
| 5,571,401 A | * 11/1996 | Lewis et al. ............... 205/787 | |
| 5,630,920 A | 5/1997 | Friese et al. | |
| 5,731,510 A | 3/1998 | Jones et al. | |

(Continued)

FOREIGN PATENT DOCUMENTS

| | | |
|---|---|---|
| DE | 4 228 052 | 4/1993 |
| DE | 4408361 | 9/1995 |
| DE | 4408504 | 9/1995 |
| DE | 201 01 638 | 4/2001 |
| EP | 293 255 | 11/1988 |

(Continued)

OTHER PUBLICATIONS

S.W. Moore, et al., A modified multilayer perceptron model for gas mixture analysis, Sensors and Actuators B, 15–16 (1993) pp. 344–348, Elsevier Sequoia.

H. Meixner, et al., Metal oxide sensors, Sensors and Actuators B 33 (1996) pp. 198–202, Elsevier Science.

(Continued)

*Primary Examiner*—Jill Warden
*Assistant Examiner*—Brian J. Sines

(57) ABSTRACT

Disclosed herein is a method and apparatus for analyzing, sensing and measuring the concentrations of various gases, including $NO_x$, hydrocarbons, carbon monoxide and oxygen, in a multi-component gas system using chemical sensors and chemical sensor arrays. The sensors and sensor arrays use chemo/electro-active materials to analyze and detect the presence of gases.

102 Claims, 3 Drawing Sheets

U.S. PATENT DOCUMENTS

| | | |
|---|---|---|
| 5,736,028 A | 4/1998 | Hjortsberg et al. |
| 5,776,601 A | 7/1998 | Fournier et al. |
| 5,832,411 A | 11/1998 | Schatzmann et al. |
| 5,879,526 A | 3/1999 | Dietz et al. |
| 6,006,586 A | 12/1999 | Yoshida et al. |
| 6,012,282 A | 1/2000 | Kato et al. |
| 6,041,592 A | 3/2000 | Huynh et al. |
| 6,082,176 A | 7/2000 | Kondo et al. |
| 6,084,418 A | 7/2000 | Takami et al. |
| 6,085,576 A | 7/2000 | Sunshine et al. |
| 6,109,095 A | 8/2000 | Addiego |
| 6,149,786 A | 11/2000 | Patrick et al. |
| 6,170,318 B1 | 1/2001 | Lewis |
| 6,235,243 B1 | 5/2001 | Fleischer et al. |
| 6,238,536 B1 | 5/2001 | Lundgren et al. |
| 6,306,351 B1 | 10/2001 | Kudo et al. |
| 6,367,320 B1 | 4/2002 | Kueper et al. |
| 6,411,905 B1 | 6/2002 | Guoliang et al. |
| 6,498,046 B2 | 12/2002 | McCarron et al. |
| 6,592,823 B1 | 7/2003 | Odermatt et al. |
| 2002/0017467 A1 | 2/2002 | Ando et al. |

FOREIGN PATENT DOCUMENTS

| | | |
|---|---|---|
| EP | 527258 | 2/1993 |
| EP | 0527 258 | 2/1993 |
| EP | 1 286 155 | 2/2003 |
| JP | 09005273 | 3/1997 |
| JP | 1006237 | 5/1998 |
| JP | 10260155 | 12/1998 |
| JP | 10267895 | 12/1998 |
| JP | 2001281185 | 3/2002 |
| WO | WO 9308467 | 4/1993 |
| WO | WO 0000808 | 1/2000 |
| WO | WO 03/087550 | 10/2003 |

OTHER PUBLICATIONS

J. Getino, et al., Integrated sensor array for gas analysis in combustion atmospheres, Sensors and Actuators B 33 (1996) pp. 128–133, Elsevier Science.

Corrado Di Natale, et al., Study of the effect of the sensor operating temperature on $SnO_2$–based sensor–array performance, Sensors and Actuators B 23 (1995) pp. 187–191, Elsevier Science.

Brent T. Marquis, et al., A semiconducting metal oxide sensor array for the detection of $NO_x$ and $NH_3$, Sensors and Actuators B 77 (2001) pp. 100–110, Elsevier Science.

G. Huyberechts, et al., Simultaneous quantification of carbon monoxide and methane in humid air using a sensor array and an artificial and an artificial neural network, Sensors and Actuators B 45 (1997) pp. 123–130, Elsevier Science.

Kazimierz Brudzewski, et al., Gas analysis system composed of a solid–state sensor array and hybrid neural network structure, Sensors and Actuators B 55 (1999) pp. 38–46, Elsevier Science.

P.C. Jurs, et al., Computational methods for the analysis of chemical sensor array data from volatile analytes, Chem Rev. 2000, 100, pp. 2649–2678, American Chemical Society.

Keith J. Albert, et al., Cross–reactive chemical sensor arrays, Chem. Rev. 2000. 100, pp. 2595–2626, American Chemical Society.

P. Vincenzini, et al., Solid state chemical and biochemical sensors, Advances in Science and Technology, 26, pp. 335–345, National Research Center, Italy.

Antonio Parado, et al., Nonlinear inverse dynamic models of gas sensing systems based on chemical sensor arrays for quantitative measurements, IEEE Transactions on Instrumentation and Measurement, vol. 47, No. 3, Jun. 1998, pp. 644–651.

BS Hoffheins, et al., Performance of simplified chemical sensor arrays in a neural network–based analytical instrument, Analysis (1992) 20, pp. 201–207, Elsevier, Paris.

Corrado Di Natale, et al., Performance evaluation of an $SnO_2$–based sensor array for the quantitative measurement of mixtures of $H_2S$ and $NO_2$, Sensors and Actuators B, 20 (1994) pp. 217–224.

H. Meixner, et al., Chemosensors for motor management systems of the future, Fresenius J. Anal. Chem. (1994) 348, pp. 536–541.

Marquis, A Semiconducting metal oxide sensor array for the detection of $NO_x$ and $NH_3$, Sensors and Actuators B 77 (2001), pp. 100–110, Orono, ME.

* cited by examiner

METHOD AND APPARATUS FOR ANALYZING MIXTURES OF GASES

This application claims the benefit of the filing date of U.S. Provisional Application No. 60/240,619, filed Oct. 16, 2000, and of U.S. Provisional Application No. 60/246,946, filed Nov. 9, 2000.

FIELD OF THE INVENTION

The present invention is a method and apparatus for sensing and analyzing certain gases, including $NO_x$, hydrocarbons, carbon monoxide and oxygen in a multi-component gas system using chemical sensors and chemical sensor arrays. The sensors and sensor arrays use chemo/electro-active materials to detect the presence of and/or calculate the concentration of individual gases within the multi-component gas system.

TECHNICAL BACKGROUND

The use of chemical sensing devices to detect certain gases is known. Many attempts have been made to find a material with selectivity and sensitivity for a specific gas. For example, U.S. Pat. No. 4,535,316 discloses a resistive sensor for measuring oxygen. See also H. Meixner et al, *Sensors and Actuators, B* 33 (1996) 198–202. It is apparent that different materials must be used for each gas to be detected. However, when a gas is part of a multi-component system, using one material to detect a specific gas is difficult because of the cross-sensitivities of the material to the various component gases of the mixture.

One example of a multi-component gaseous system is a combustion gas emission, which can include oxygen, carbon monoxide, nitrogen oxides, hydrocarbons, $CO_2$, $H_2S$, sulfur dioxide, hydrogen, water vapor, halogens and ammonia. See H. Meixner et al, Fresenius' *J. Anal. Chem.,* 348 (1994) 536–541. In many combustion processes, there is a need to determine whether the gas emissions meet requirements established by federal and state air quality regulations in various jurisdictions. Several types of gas sensors have been developed to address this need. See U.S. Pat. No. 5, 630,920, Friese et al, which discloses an electrochemical oxygen sensor; U.S. Pat. No. 4,770,760, Noda et al, which discloses a sensor for detecting oxygen and oxides of nitrogen; and U.S. Pat. No. 4,535,316, which discloses a resistive sensor for measuring oxygen. It would be advantageous to be able to simultaneously analyze two or more components of a mixture such as a combustion gas emission, to calculate concentration for example, in terms only of data generated by direct contact of the gases with a sensor and without having to separate any of the gases in the mixture. Prior art methods do not currently meet this need.

Numerous sensors have been disclosed to detect gases evolving from foods and from other relatively low temperature applications. See K. Albert et al, *Chem. Rev.,* 200 (2000) 2595–2626. Arrays of several undoped and doped tin oxide sensors have also been disclosed for use in detecting various combustion gases up to 450° C. See C. Di Natale et al, *Sensors and Actuators,* B 20 (1994) 217–224; J. Getino et al, *Sensors and Actuators,* B33 (1996) 128–133; and C. Di Natale et al, *Sensors and Actuators,* B 23 (1995) 187–191. However, at higher temperatures and in the highly corrosive environment in which one would use chemical sensors to monitor combustion gases, operating temperature can alter or impair the performance of the sensor array. That being the case, high temperature environments require the use of materials that are both chemically and thermally stable and that maintain measurable responses to the gases of interest. The effect of the operating temperature on the response of tin oxide bases sensor arrays was studied up to 450° C. See C. Di Natale, *Sensors and Actuators B*23 (1995) 187–191. However, materials in addition to those previously known in the art are still needed to be able to provide a method and apparatus capable of directly monitoring the gas emissions of multi-component gas systems at higher temperatures, such as would be encountered in the operation of combustion gas systems.

Addressing this need would permit the use of a chemical sensor to measure combustion emissions, such as automobile exhausts, and determine whether those emissions meet functional and mandated requirements. In addition, it has surprisingly been found that the method and apparatus of this invention that are useful for analyzing high temperature gases, such as automotive emissions, may be employed with equal effect in analyzing low temperature gases.

SUMMARY OF THE INVENTION

This invention provides a method for directly sensing gas components in a multi-component gas system, comprising the steps of: (i) exposing a chemical sensor comprising an array of at least two chemo/electro-active materials to a multi-component gas system, detecting a response, and directly measuring the response of each chemo/electro-active material. Preferably the chemo/electro-active material is a semiconducting material, and the multi-component gas system is a combustion process emission. The response that is measured can be a measurement of capacitance, voltage, current, AC impedance, or DC resistance.

This invention also provides a chemical sensor for directly sensing the presence of gas components in a multi-component gas system, comprising a substrate; an array of at least two chemo/electro-active materials on said substrate; and a means for detecting a response from said chemo/electro-active materials when exposed to said analyte gas component(s) in the system. Preferably the chemo/electro-active material is a semiconducting material, and the multi-component gas system is a combustion process emission. The response that is detected can be an electrical property such as capacitance, voltage, current, AC impedance, or DC resistance. The device can additionally contain a housing, means for measuring the detected responses, and means for analyzing the results of the measured responses in order to identify the presence and/or concentrations of the analyte gas components(s).

This invention also provides for a chemical sensor device for directly sensing the presence and/or concentration of gas component(s) in a multi-component gas system, comprising: a substrate; an array of at least two chemo/electro-active materials deposited on said substrate; a means for detecting a change in electrical properties of said chemo/electro-active materials upon exposure to said multi-component gas component(s); means for analyzing the results of the detected changes in electrical properties in order to identify the presence and/or concentrations of said gas component(s); and a housing. The chemo/electro-active materials may be semiconducting materials.

In another embodiment, this invention involves an apparatus for analyzing at least one individual gas component in a multi-component gas mixture, containing:

(a) an array of at least two chemo/electro-active materials connected in parallel circuitry, each chemo/electro-active material exhibiting a different electrical response characteristic upon exposure to the individual gas component than each other chemo/electro-active material;

(b) means for determining an electrical response of each chemo/electro-active material upon exposure of the array to the gas mixture;

(c) means for determining a value for the temperature of the array connected in parallel circuitry with the chemo/electro-active materials; and (d) means for digitizing the electrical responses and the temperature value, and calculating a value from the digitized electrical responses and temperature value, to perform an analysis of the individual gas component.

In a further embodiment, this invention involves, in a multi-component gas mixture having a temperature of about 400° C. or more, an apparatus for calculating the concentration of at least two individual analyte gas components in the mixture, containing:

(a) an array of at least three chemo/electro-active materials, the array being situated within the gas mixture, and each chemo/electro-active material having a different electrical response characteristic upon exposure to each of the individual analyte gas components than each of the other chemo/electro-active materials;

(b) means for determining an electrical response of each chemo/electro-active material upon exposure of the array to the unseparated components of the gas mixture; and (c) means for calculating the concentration of each of the individual analyte gas components from the electrical responses of the chemo/electro-active materials upon exposure to the multi-component gas mixture only.

In yet another embodiment, this invention involves, in a multi-component gas mixture having a temperature of about 400° C. or more, an apparatus for calculating the concentration of at least two individual analyte gas components in the mixture, containing:

(a) an array of at least three chemo/electro-active materials connected in parallel circuitry, the array being situated within the gas mixture, and each chemo/electro-active material exhibiting a change in electrical resistance upon exposure to each of the individual analyte gas components, wherein at least one chemo/electro-active material, when at a temperature of about 400° C. or more, (i) has an electrical resistivity in the range of about 1 ohm-cm to about $10^5$ ohm-cm, and (ii) exhibits a change in electrical resistance of at least about 0.1 percent upon exposure of the material to an analyte gas component, as compared to the resistance before exposure;

(b) means for determining the change in resistance of each chemo/electro-active material upon exposure of the array to the gas mixture; and (c) means for calculating the concentration of each of the individual analyte gas components from the changes in resistance of the chemo/electro-active materials.

In yet another embodiment, this invention involves an apparatus for analyzing at least one individual gas component in a multi-component gas mixture, containing:

(a) an array of at least two chemo/electro-active materials, each chemo/electro-active material having a different electrical response characteristic upon exposure at a selected temperature to the individual gas component than each of the other chemo/electro-active materials, the electrical response characteristic of each material being quantifiable as a value, wherein the response value of at least one material is constant or varies by no more than about twenty percent during exposure of the material to an individual gas component at the selected temperature for a period of at least about one minute;

(b) means for determining the electrical response value of each chemo/electro-active material upon exposure of the array to the gas mixture; and (c) means for performing an analysis of the individual gas component from the electrical response values.

In yet another embodiment, this invention involves, in a multi-component gas mixture having a temperature of less than about 400° C., an apparatus for analyzing at least one individual gas component in the mixture, containing:

(a) an array of at least two chemo/electro-active materials, each chemo/electro-active material having a different electrical response characteristic upon exposure at a selected temperature to the individual gas component than each of the other chemo/electro-active materials, the array being situated within the gas mixture and having a substantially constant temperature of about 400° C. or more;

(b) means for determining the electrical response value of each chemo/electro-active material upon exposure of the array to the gas mixture; and (c) means for performing an analysis of the individual gas component from the electrical response values.

In yet another embodiment, this invention involves an apparatus for analyzing at least one individual gas component in a multi-component gas mixture, containing:

(a) an array of first and second chemo/electro-active materials, each chemo/electro-active material having a different electrical response characteristic upon exposure at a selected temperature to the individual gas component than each of the other chemo/electro-active materials, wherein the chemo/electro-active materials are selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$; and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1, provided that a+b+c=1; and x is a number sufficient so that the oxygen present balances the charges of the other elements in the compound;

(b) means for determining the electrical response of each chemo/electro-active material upon exposure of the array to the gas mixture; and (c) means for performing an analysis of the individual gas component from the electrical responses.

In yet another embodiment, this invention involves a method for analyzing at least one individual gas component in a multi-component gas mixture, including the steps of:

(a) providing an array of at least two chemo/electro-active materials connected in parallel circuitry, each chemo/electro-active material exhibiting a different electrical response characteristic upon exposure to the individual gas component than each other chemo/electro-active material;

(b) exposing the array to the gas mixture;

(c) determining an electrical response of each chemo/electro-active material upon exposure of the array to the gas mixture;

(d) determining a value for the temperature of the gas mixture independently of the determination of the electrical responses of the chemo/elctro-active materials; and (e) digitizing the electrical responses and the temperature value, and calculating a value from the digitized electrical responses and temperature value to perform an analysis of the individual gas component.

In yet another embodiment, this invention involves a method for calculating the concentration of at least two individual analyte gas components in a multi-component gas mixture having a temperature of about 400° C. or more, including the steps of:

(a) providing within the gas mixture an array of at least three chemo/electro-active materials, each chemo/electro-active material having a different electrical response characteristic upon exposure to each of the individual analyte gas components than each of the other chemo/electro-active materials, wherein at least one chemo/electro-active material, when at a temperature of about 400° C. or more, (i) has an electrical resistivity in the range of about 1 ohm-cm to about $10^5$ ohm-cm, and (ii) exhibits a change in electrical resistance of at least about 0.1 percent upon exposure of the material to an analyte gas component, as compared to the resistance before exposure;

(b) determining an electrical response of each chemo/electro-active material upon exposure of the array to the unseparated components of the gas mixture; and (c) calculating the concentration of each of the individual analyte gas components from the electrical responses of the chemo/electro-active materials upon exposure to the multi-component gas mixture only.

In yet another embodiment, this invention involves a method for analyzing at least one individual gas component in a multi-component gas mixture, including the steps of:

(a) providing an array of at least two chemo/electro-active materials, each chemo/electro-active material having a different electrical response characteristic upon exposure at a selected temperature to the individual gas component than each of the other chemo/electro-active materials, the electrical response characteristic of each material being quantifiable as a value, wherein the response value of at least one material is constant or varies by no more than about twenty percent during exposure of the material to an individual gas component at the selected temperature for a period of at least about one minute;

(b) determining the electrical response value of each chemo/electro-active material upon exposure of the array to the gas mixture; and (c) performing an analysis of the individual gas component from the electrical response values.

DETAILED DESCRIPTION OF THE INVENTION

The present invention is a method and apparatus for directly sensing one or more analyte gases in multi-component gas systems under variable temperature conditions. By "directly sensing" is meant that an array of gas-sensing materials will be exposed to a mixture of gases that constitutes a multi-component gas system, such as in a stream of flowing gases. The array may be situated within the gas mixture, and more particularly within the source of the gas mixture, if desired. Alternatively, the array may reside in a chamber to which the gas mixture is directed from its source at another location. The gas mixture may be inserted in and removed from the chamber by piping, conduits or any other suitable gas transmission equipment.

A response may be obtained upon exposure of the gas-sensing materials to the multi-component gas mixture, and the response will be a function of the concentrations of one or more of the analyte gases themselves in the gas mixture. The sensor materials will be exposed substantially simultaneously to each of the analyte gases, and the analyte gas(es) do not have to be physically separated from the multi-component gas mixture in order to be analyzed. This invention can be used, for example, to detect and/or measure the concentrations of combustion gases, such as oxygen, carbon monoxide, nitrogen oxides, hydrocarbons such as butane, $CO_2$, $H_2S$, sulfur dioxide, halogens, hydrogen, water vaopr and ammonia, at variable temperatures in automobile emissions.

This invention is therefore useful at the higher temperatures found in automotive emission systems, typically in the range of from about 400° C. to about 1000° C. In addition there are a variety of other combustion processes for which this invention could be applied, including diesel engines and home heating. These applications require the detection of gases such as nitrogen oxides, ammonia, carbon monoxide, hydrocarbons and oxygen at the ppm to percent levels, typically in a highly corrosive environment. This invention is also useful for detecting gases in other gas systems such as those found in manufacturing processes, waste streams, and environmental monitoring; or in systems in which odor detection important and/or which are at lower temperature, such as in the medical, agricultural or food and beverage industries.

Figure 1:
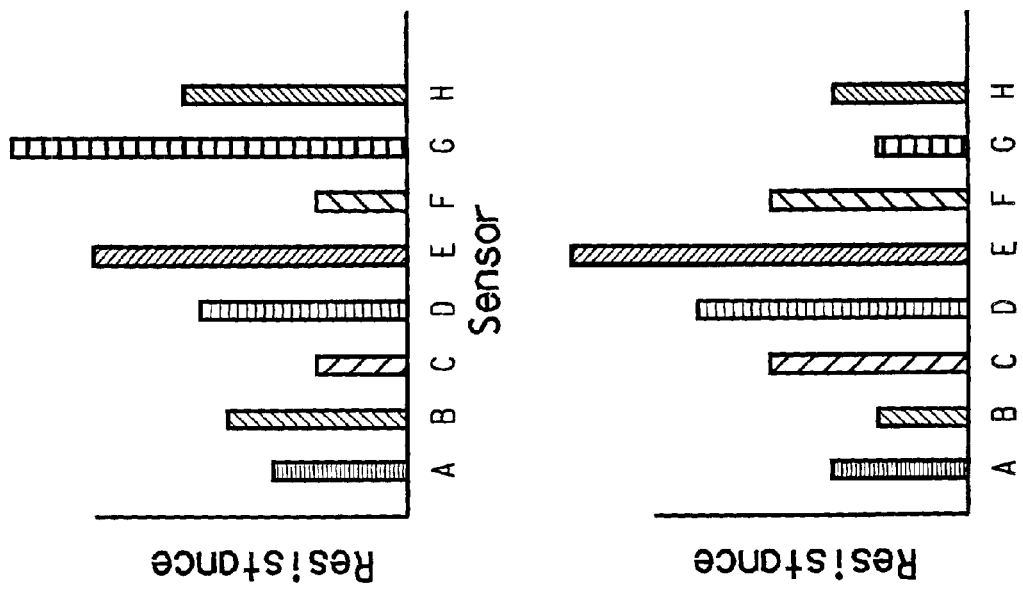
FIG. 1 depicts the sensor array concept.
Figure 1:
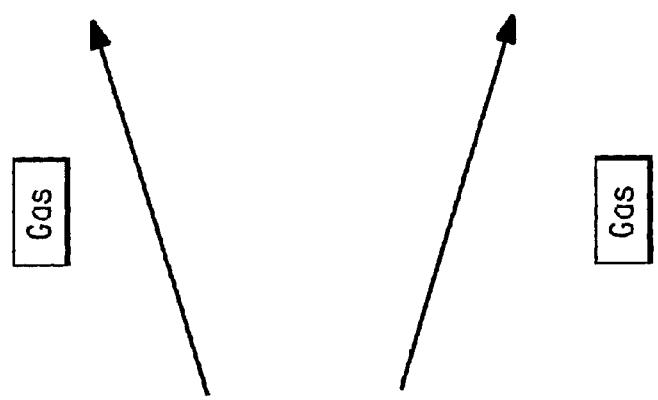
Figure 1:
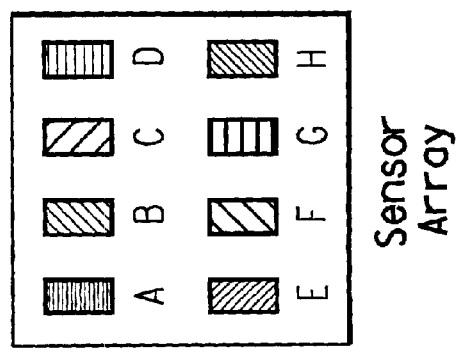

This invention utilizes an array of sensing materials to analyze the components of a gas system to, for example, detect the presence of and/or calculate the concentration of one or more individual analyte gas components in the system. By "array" is meant at least two different materials that are spatially separated, as shown for example in FIG. 1. The array may contain, for example, 3, 4, 5, 6, 8, 10 or 12, or other desirable numbers of, gas-sensing materials. It is preferred that there be provided at least one sensor material for each of the individual gases in the mixture to be analyzed. Preferably the mole percentages of the major components of each gas-sensing material differs from that of each of the others.

The sensing materials used are chemo/electro-active materials. A "chemo/electro-active material" is a material that has an electrical response to at least one particular gas. Some metal oxide semiconducting materials, mixtures thereof, or mixtures of metal oxide semiconductors with other inorganic compounds are chemo/electro-active, and are particularly useful in this invention. Each of the various chemo/electro-active materials used herein preferably exhibits an electrically-detectable response of a different kind and/or extent upon exposure to an analyte gas of interest than each of the other chemo/electro-active materials. As a result, an array of appropriately chosen chemo/electro-active materials can be used to analyze a multi-component gas mixture, such as by interacting with an analyte gas, sensing an analyte gas, or determining the presence and/or concentration of one or more analyte gases in a gas stream, despite the presence of interfering gases that are not of interest.

This invention is useful for detecting those gases that are expected to be present in the gas stream. For example, in a combustion process, gases that are expected to be present include oxygen, nitrogen oxides, carbon monoxide, hydrocarbons, ammonia or hydrogen sulfide. Other gases of interest may include alcohol vapors, solvent vapors, hydrogen, water vapor, and those deriving from saturated and unsaturated hydrocarbons, ethers, ketones, aldehydes, carbonyls, biomolecules and microorganisms.

The measurement of gas concentrations using these sensor materials can be based on a change in an electrical property, such as AC impedance, of each of the materials upon exposure of the materials to a mixture containing one or more analyte gases. Analysis of a gas mixture can also be performed in terms of extent of change in other electrical properties of the sensor materials, such as capacitance, voltage, current or DC resistance. Change in DC resistance may be determined, for example, by measuring change in temperature at constant voltage. The change in one of these illustrative properties of a sensor material is a function of the partial pressure of an analyte gas within the gas mixture, which in turn determines the concentration in which the molecules of the analyte gas become adsorbed on the surface of a sensor material, thus affecting the electrical response characteristics of that material. By using an array of chemo/electro-active materials, a pattern of the respective responses exhibited by the materials upon exposure to one or more analyte gas can be used to simultaneously and directly detect the presence of, and/or measure the concentration of, at least one gas in a multi-component gas system. The invention, in turn, can be used to determine the composition of the gas system. The concept is illustrated schematically in FIG. 1 and is exemplified below.

To illustrate, consider the theoretical example below where a response is obtanied, which is depicted as positive (+), or no response is obtained, which is depicted as negative (−). Material 1 responds to Gas 1 and Gas 2, but shows no response to Gas 3. Material 2 responds to Gas 1 and Gas 3, but shows no response to Gas 2, and Material 3 responds to Gas 2 and Gas 3, but shows no response to Gas 1.

|  | Material 1 | Material 2 | Material 3 |
|---|---|---|---|
| Gas 1 | + | + | − |
| Gas 2 | + | − | + |
| Gas 3 | − | + | + |

Therefore, if an array consisting of Materials 1, 2 and 3 gives the following response to an unknown gas,

|  | Material 1 | Material 2 | Material 3 |
|---|---|---|---|
| Unknown Gas | + | − | + | then the unknown gas would be identified as Gas 2. The response of each material would be a function of the partial pressure within the mixture of, and thus the concentration of, the analyte gas; and the reponse could be recorded as a numerical value. In such case, the numerical values of the responses can be used to give quantitative information on the concentration within the mixture of the analyte gas. In a multicomponent gas system, chemometrics, neural networks or other pattern recognition techniques could be used to calculate the concentration of one or more anylayte gases in the mixture of the system.

The chemo/electro-active material can be of any type, but especially useful are semiconducting metal oxides such as ZnO, TiO$_2$, WO$_3$, and SnO$_2$. These particular materials are advantageous due to their chemical and thermal stability. The semiconducting material can be a mixture of a semiconducting material with other semiconducting materials, or with any inorganic material, or combinations thereof. The semiconducting materials of interest can be deposited on a suitable solid substrate that is an insulator such as, but not limited to, alumina or silica and is stable under the conditions of the multi-component gas mixture. The array then takes the form of the sensor materials as deposited on the substrate. Other suitable sensor materials include single crystal or polycrystalline semiconductors of the bulk or thin film type, amorphous semiconducting materials, and semiconductor materials that are not composed of metal oxides.

The chemo/electro-active materials used as sensor materials in this invention may, for example, be metal oxides of the formula $M^1O_x$, $M^1_aM^2_bO_x$, or $M^1_aM^2_bM^3_cO_x$; or mixtures thereof, wherein $M^1$, $M^2$ and $M^3$ are metals that form stable oxides when fired in the presence of oxygen above 500° C.;

$M^1$ is selected from Periodic Groups 2–15 and the lanthanide group;

$M^2$ and $M^3$ are independently selected from Periodic Groups 1–15 and the lanthanide group;

a, b, and c are each independently in the range of about 0.0005 to about 1, provided that a+b+c=1; and x is a number sufficient so that the oxygen present balances the charges of the other elements in the compound.

The metal oxides that contain more than one metal do not have to be a compound or solid solution, but can be a mixture of discrete metal oxides. They may exhibit composition gradients, and can be crystalline or amorphous. Suitable metal oxides are those that are 1) when at a temperature of about 400° C. or above, have a resistivity of about 1 to about $10^5$ ohm-cm, and preferably about 10 to about $10^4$ ohm-cm, 2) show a chemo/electro response to at least one gas of interest, and 3) are stable and have mechanical integrity, that is are able to adhere to the substrate and not degrade at the operating temperature.

The metal oxides may also contain minor or trace amounts of hydration and elements present in the precursor materials.

In certain preferred embodiments, the metal oxide materials may include those in which $M^1$ is selected from the group consisting of Ce, Co, Cu, Fe, Ga, Nb, Ni, Pr, Ru, Sn, Ti, Tm, W, Yb, Zn, and Zr; and/or $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$.

In certain other preferred embodiments, the metal oxide materials may include those in which $M^1O_x$ is $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive; and/or $M^1{}_aM^2{}_bO_x$ is $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, or $Ta_aTi_bO_x$ with frit additive;

and/or $M^1{}_aM^2{}_bM^3{}_cO_x$ is $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

In certain other preferred embodiments, the metal oxide materials may include those which are in an array of first and second chemo/electro-active materials, wherein the chemo/electro-active materials are selected from the pairings in the group consisting of (i) the first material is $M^1O_x$, and the second material is $M^1{}_aM^2{}_bO_x$;

(ii) the first material is $M^1O_x$, and the second material is $M^1{}_aM^2{}_bM^3{}_cO_x$;

(iii) the first material is $M^1{}_aM^2{}_bO_x$, and the second material is $M^1{}_aM^2{}_bM^3{}_cO_x$;

(iv) the first material is a first $M^1O_x$, and the second material is a second $M^1O_x$;

(v) the first material is a first $M^1{}_aM^2{}_bO_x$, and the second material is a second $M^1{}_aM^2{}_bO_x$; and (vi) the first material is a first $M^1{}_aM^2{}_bM^3{}_cO_x$, and the second material is a second $M^1{}_aM^2{}_bM^3{}_cO_x$;

wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$; a, b and c are each independently about 0.0005 to about 1, provided that a+b+c=1; and x is a number sufficient so that the oxygen present balances the charges of the other elements in the compound.

The sensor materials may optionally contain one or more additives to promote adhesion or to alter the conductance, resistance or selectivity thereof. Examples of additives to promote adhesion are frits, which are finely ground glass, or finely ground inorganic minerals that are transformed into glass or enamel on heating. Illustrative frits include those designated as F2834, F3876, F2967, KH770, KH710 and KH375, available from DuPont Technologies. These may be used in amounts of up to 30 volume percent of the composition from which the sensor material is made. Examples of additives to alter the conductance, resistance or selectivity include Ag, Au or Pt as well as frits. If desired, the sensor materials may also contain additives, for example, that catalyze the oxidation of a gas of interest or promote the selectivity for a particular analyte gas, or other dopants that convert an n semiconductor to a p semiconductor, or vice versa. These additives may be used in amounts of up to 30 weight percent of the composition from which the sensor material is made. Any frits or other additives used need not be uniformly or homogeneously distributed throughout the sensor material, but may be localized on or near a particular surface thereof as desired.

Any method of depositing the chemo/electro-active material to the substrate is suitable. One technique used for deposition is applying the semiconducting material on an alumina substrate on which electrodes are screen printed. The semiconducting material can be deposited on top of electrodes by hand painting semiconducting materials onto the substrate, nanopipetting materials into wells, thin film deposition, or thick film printing techniques. Most techniques are followed by a final firing to sinter the semiconducting materials.

Figure 2:
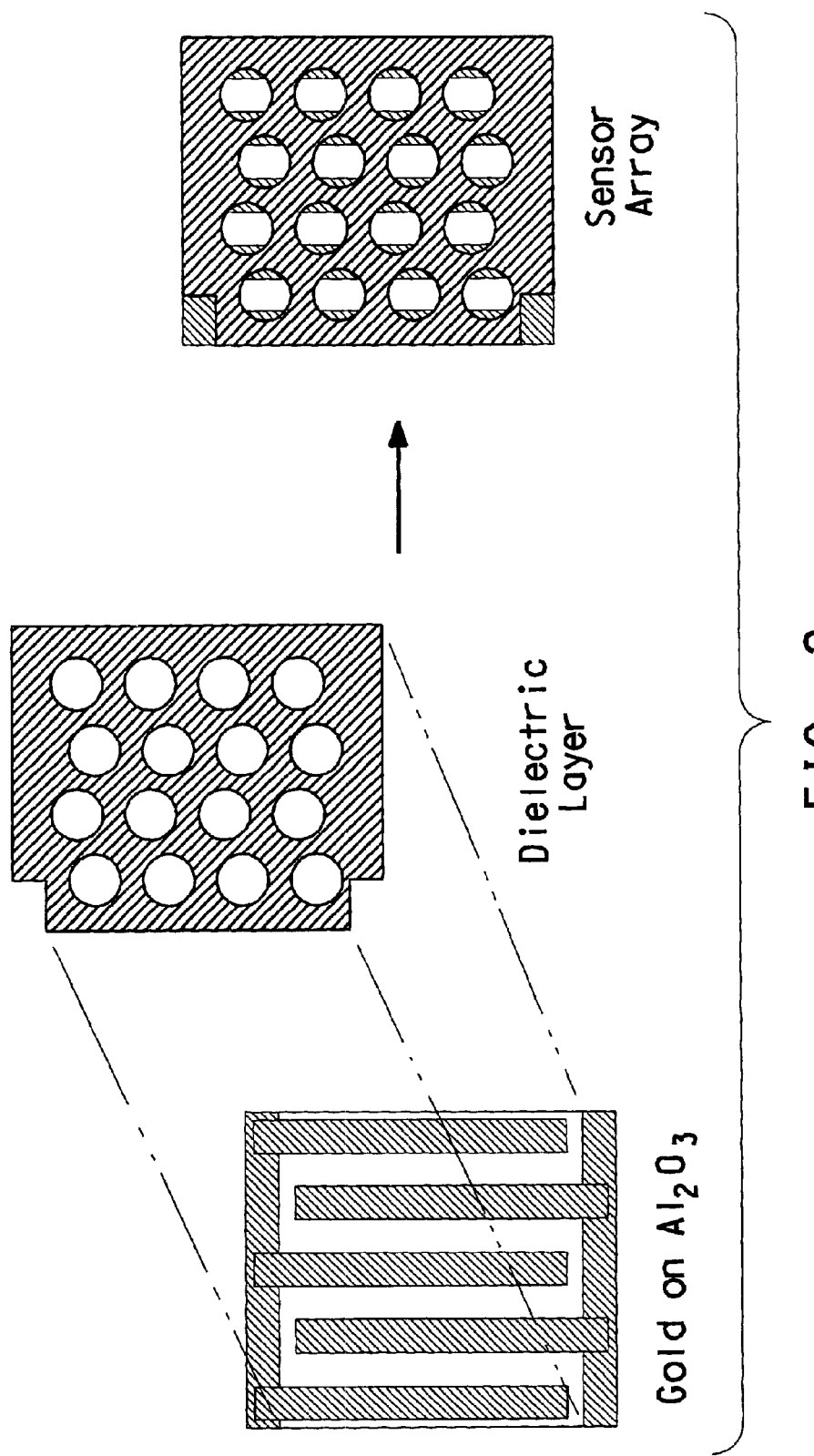
FIG. 2 is a schematic of the pattern of interdigitated electrodes overlaid with the dielectric overlayer, forming sixteen blank wells.
Figure 3A:
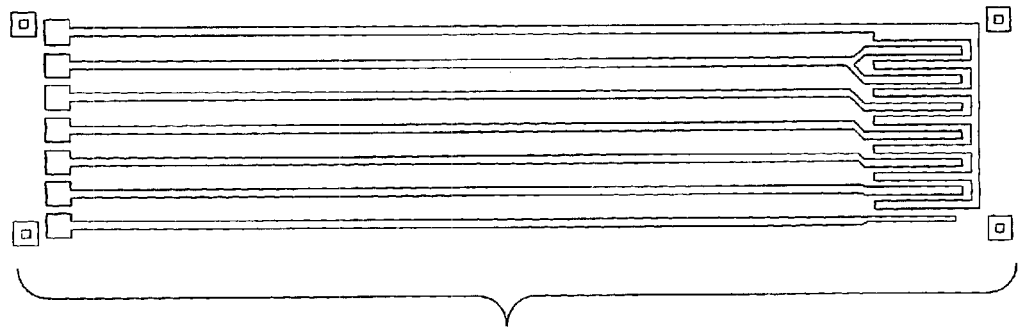
FIG. 3 depicts the electrode pattern, dielectric pattern, and sensor material pattern used in preparing array chips for measurement.
Figure 3B:
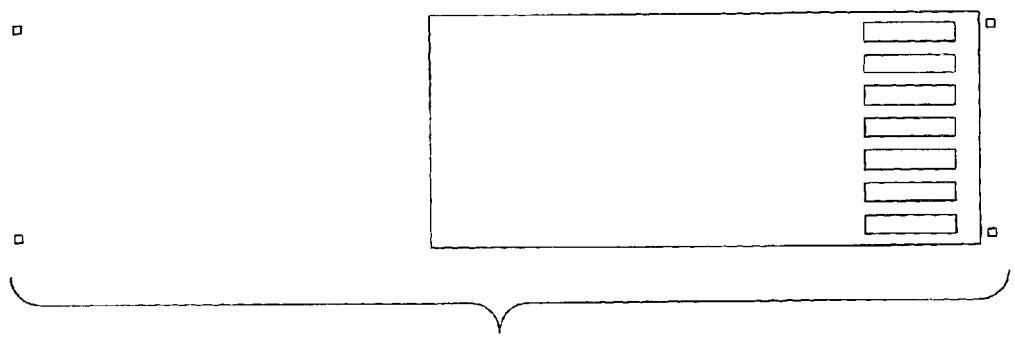
Figure 3C:
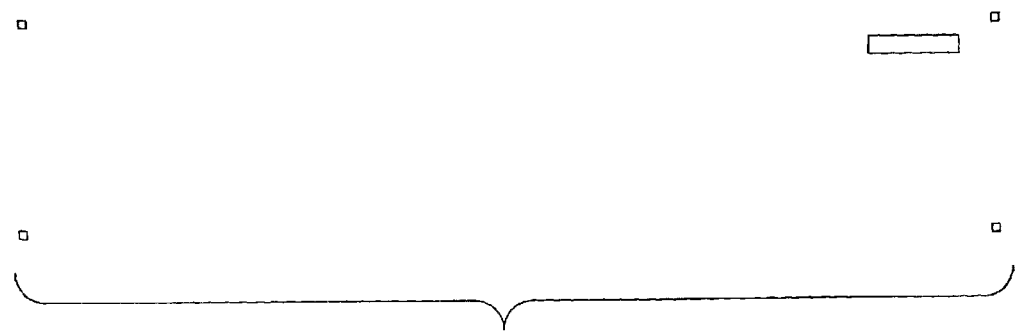

Techniques for screen-printing substrates with the electrodes and chemo/electro-active materials are illustrated in FIGS. 2–3. FIG. 2 depicts a method of using interdigitated electrodes overlaid with dielectric material, forming blank wells into which the chemo/electro-active materials can be deposited. FIG. 3 depicts an electrode screen pattern for an array of 6 materials which is printed on both sides of the substrate to provide for a 12-material array chip. Two of the electrodes are in parallel so it holds only 6 unique materials. Below that is the screen pattern for the dielectric material, which is screen printed on top of the electrodes on both side of the substrate to prevent the material from being fouled by contact with the gas mixture, such as becoming covered with soot from an auto, truck, machine or equipment engine, and shorting out. Below that is the screen pattern for the actual sensor materials. This is printed in the holes in the dielectric on top of the electrodes. When more than one material is used in the array the individual materials are printed one at a time.

The sensor materials are interconnected by conductors, and those conductors are in turn connected to electrical input and output circuitry. The circuitry includes meters, data acquisition means and other devices as appropriate to measure and record the response exhibited by a sensor material upon exposure to an analyte gas, to generate a signal in relation to that response, and to process the signals in a manner that completes the quantitative analysis of the gas mixture by presenting a report or display of a result indicating the presence and/or concentration of the analyte gas. For example, the several sensors in an array may be accessed serially by a multiplexer, and the data retrieved may then be processed on the basis of the proportionality of the value of an electrical property measured to the concentration of an individual analyte gas in a multi-component mixture. The data acquisition, processing, storage and display system may include means for conversion from analog to digital format to enable the digitization of the responses of the sensors and other values, such as the measurement of temperature.

A response model is constructed using equations in which constants, coefficients or other factors are derived from pre-determined values characteristic of a precisely measured electrical response of an individual sensor material to a particular individual gas expected to be present as a component in the mixture to be analyzed. The equation may be constructed in an manner that takes temperature into account as a value separate and apart from the electrical responses exhibited by the sensor materials upon exposure to the gas mixture. Each individual sensor material in the array differs from each of the other sensors in its response to at least one of the component gases in the mixture, and the responses of each of the sensors to each analyte gas by itself is known.

The gas of interest to which the chemo/electro-active material will be exposed can be a single gas, a mixture, or one or more gases mixed with an inert gas such as nitrogen. Particular gases of interest are donor and acceptor gases. These are gases that either donate electrons to the semiconducting material, such as carbon monoxide, $H_2S$ and hydrocarbons, or accept electrons from the semiconducting material, such as $O_2$ nitrogen oxides (commonly depicted as $NO_x$), and halogens. When exposed to a donor gas, an n-type semiconducting material will have a decrease in electrical resistance, increasing the current, and it, therefore, will show an increase in temperature due to $I^2R$ heating. When exposed to an acceptor gas, an n-type semiconducting material will have an increase in electrical resistance, decreasing the current, and therefore will show a decrease in temperature due to $I^2R$ heating. The opposite occurs with p-type semiconducting materials.

The geometry of the sensor materials, selection of material, thickness of material, and voltages used can vary and depend on the sensitivity required. The sensor materials are preferably connected in parallel in a circuit to which a voltage of about 1 to about 20, preferably about 1 to about 12, volts is applied across the sensor materials. When performing an analysis of a muti-component gas mixture, it is preferred that each chemo/electro-active sensor material in the array exhibit a different electrical response characteristic than each of the other chemo/electro-active materials in the array upon exposure to an analyte gas component of interest in the mixture.

As noted, the types of electrical response characteristics that may be measured include AC impedance or resistance, capacitance, voltage, current or DC resistance. It is preferred to use resistance as the electric response characteristic of the sensor materials that is measured to perform analysis of a component within the gas mixture. For example a suitable sensor material may be that which, when at a temperature of about 400° C. or above, has a resistivity of at least about 1 ohm-cm, and preferably at least about 10 ohm-cm, and yet no more than about $10^5$ ohm-cm, and preferably no more than about $10^4$ ohm-cm. Such a sensor material may also be characterized as that which exhibits, preferably at a temperature of about 400° C. or above, upon exposure to an analyte in the gas mixture, a change in resistance of at least about 0.1 percent, and preferably at least about 1 percent, as compared to the resistance before exposure.

Regardless of the type of response characteristic that is measured for the purpose of analyzing the gaseous component(s) of interest, it is desirable that a sensor material be utilized for which that response value is stable over an extended period of time. When the sensor material is exposed to the analyte, the concentration of the analyte being a function of the composition of the particular gas mixture in which it is contained, the response characteristic of the sensor material will preferably remain constant or vary to only a small extent over an extended period of time at a constant temperature. For example, the response characteristic, if it varies, will vary by no more than about twenty percent, preferably no more than about ten percent, more preferably no more than about five percent, and most preferably no more than about one percent over a period of at least about 1 minute, or preferably a period of hours such as at least about 1 hour, preferably at least about 10 hours, more preferably at least about 100 hours, and most preferably at least about 1000 hours. One of the advantages of the sensor materials described above is that they are characterized by this kind of stability of response.

In applications in which the gas mixture is above about 400° C., the temperature of the sensor materials and the array may be determined substantially only, and preferably is determined solely, by the temperature of the gas mixture in which the analyste gas(es) are contained. This is typically a variable temperature. When higher-temperature gases are being anaylzyed, it may be desirable to provide a heater with the array to bring the sensor materials quickly to a minimum temperature. Once the analysis has begun, however, the heater (if used) is typically switched off, and no method is provided to maintain the sensor materials at a preselected temperature. The temperature of the sensor materials thus rises or falls as does the temperature of the surrounding environment. The temperature of the surrounding environment, and thus the sensors and the array, is determined by (or results from) substantially only the temperature of the gas mixture to which the array is exposed.

In applications in which the gas mixture is below about 400° C., it may be preferred to maintain the sensor materials and the array at a preselected temperature of about 400° C. or above. This preselected temperature may be substantially constant, or preferably is constant. The preselected temperature may also be about 500° C. or above, about 600° C. or above, or about 700° C. or above. This may be conveniently done with a heater incorporated with the array, in a manner as known in the art. The temperature of the gas mixture may also be below about 300° C., below about 200° C., or below about 100° C.

A change of temperature in the array may be indicated by a change in the quantified value of the electrical response characteristic, resistance for example, of a sensor material. At a constant partial pressure in the mixture of a gas of interest, the electrical response characteristic of a sensor material may vary with a change in temperature of the array, and thus the material. This change in the value of the electrical response characteristic may be measured for the purpose of determining or measuring the extent of change of, and thus a value for, temperature. It is preferred that this measurement of temperature be made independently of the determination of the electrical responses of the chemo/electro-active materials. This can be done by connecting the temperature measuring device in parallel circuitry with the sensor materials, rather than in series. A thermocouple or a pyrometer is useful for the purpose of determining the temperature of the array. Particularly if the termperature determining device is a thermistor, typically a material that is not responsive to an analyte gas, the thermistor is preferably made from a different material than the material from which any of the gas sensors is made. Regardless of the method by which temperature or change in temperature is determined, a temperature value or a quantified change in temperature is a desirable input, preferably in digitized form, from which an analysis of an analyte gas in a mixture of gases may be performed.

Unlike various prior-art technologies, in the method and apparatus of this invention, there is no need to separate the component gases of the mixture for purposes of performing an analysis, such as by a membrane or electrolytic cell. There is also no need when performing an analysis by means of this invention to employ a reference gas, to bring the response or analytical results back to a base line value. With the exception of preliminary testing to determine a standardized response value to be assigned to the exposure of each individual sensor material to each individual analyte gas. The sensor materials are exposed only to the mixture that contains an analyte gas component. The sensor materials are not exposed to any other gas to obtain response values for comparison to those obtained from the analyte. The analysis of the component gas(es) of interest is therefore performed only from the electrical responses obtained upon exposure of the chemo/electro-active materials to the mixture containing the analyte. No information about an anyalte gas is inferred by exposure of the sensor materials to any gas other than the analyte itself as contained within the mixture.

This invention therefore provides a method and apparatus for directly sensing the presence and/or concentration of one or more gases in an multi-component gas system, comprising an array of at least two chemo/electro-active materials chosen to detect the gases in a multi-component gas stream. The array, gas of interest, gas stream, and chemo/electro-active materials are as described above. The multi-component gas system can be at essentially any temperature that is not so low or so high that the sensor materials are degraded or the sensor apparatus otherwise malfunctions. In one embodiment, the gas system may be at a lower temperature such as room temperature (about 25° C.) or elsewhere in the range of about 0° C. to less than about 100° C., whereas in another embodiment the gas mixture may at a higher temperature such as in the range of about 400° C. to about 1000° C.

The invention is applicable to gas mixtures that may be at higher temperatures—gases for example in combustion streams such as automobile exhausts, diesel engines and home heating systems. The invention is also applicable, however, to gas mixtures derived from other sources, such as in manufacturing processes, waste streams, and environmental monitoring; or in systems in which odor detection is important and/or which are at lower temperature, such as in the medical, agricultural or food and beverage industries. The gas mixture may therefore have a temperature that is about 100° C. or more, about 200° C. or more, about 300° C. or more, about 400° C. or more, about 500° C. or more, about 600° C. or more, about 700° C. or more, or about 800° C. or more, and yet is less than about 1000° C., is less than about 900° C., is less than about 800° C., is less than about 700° C., is less than about 600° C., is less than about 500° C., is less than about 400° C., is less than about 300° C., is less than about 200° C., or is less than about 100° C.

This invention will further comprise means to determine, measure and record responses exhibited by each of the chemo/electro-active materials present upon exposure to the gas mixture. For example, any means that will determine, measure and record changes in electrical properties can be used. This may, for example, be a device that is capable of measuring the change in AC impedance of the materials in response to the concentration of adsorbed gas molecules at their surfaces. Other means for determining electrical properties can be suitable devices used to measure, for example, capacitance, voltage, current or DC resistance. Alternatively a change in temperature of the sensing material may be measured and recorded. The chemical sensing method and apparatus may further comprise a means to measure or analyze the detected gases such that the presence of the gases are identified and their concentrations are measured. These means can include devices, such as instrumentation or equipment that is capable of performing chemometrics, neural networks or other pattern recognition techniques. The chemical sensor device will further comprise a housing for the array of chemo/electro-active materials, the means for detecting, and a means for analyzing.

The invention also provides a chemical sensor for directly sensing the presence and/or concentration of one or more gases in an multi-component gas system, said sensor comprising: a substrate, an array of at least two chemo/electro-active materials chosen to detect the predetermined gases in a multi-component gas stream, and a means to detect changes in electrical properties in each of the chemo/electro-active materials present upon exposure to the gas system. The array, gas of interest, gas stream, chemo/electro-active materials, and means for detecting are as described above.

The array of sensor materials should be able to detect an individual gas of interest despite competing reactions caused by the presence of the several other components of the multi-component mixture. For this purpose, this invention uses a an array of multiple sensor materials, as described herein, each of which has a different sensitivity for at least one of the gas components of the mixture to be detected. A sensors that has the needed sensitivity, that has the other attributes described herein, and that can operate in the types of conditions described herein, is obtained by selection of appropriate compositions of materials from which the sensor is made. Various suitable compositions of materials for this purpose are described herein. The number of sensors in the array is typically greater than or equal to the number of individual gas components to be analyzed in the mixture.

The following non-limiting examples are meant to illustrate the invention but are not intended to limit it in any way. In the examples provided below, "chip" is used to describe an alumina substrate comprising an electrode and sensing material, and dielectric, if a dielectric is used. The notation "X % A:MO" means that another inorganic compound (A) has been added at the specified concentration (X % on an atomic basis) to the metal oxide (MO). The term "frit" is used to describe a mixture of inorganic compounds that usually form a glass at some temperature.

EXAMPLES

Described below are exemplary techniques that may be used to prepare sensor materials, and to measure signals using infrared (IR) thermographic and AC impedance techniques.

IR Thermographic Samples and Measurements

The change in impedance of a sensor material when exposed to a gas or gas mixture may be determined by measuring the change in temperature of the material sample by a technique such as infrared thermographic imaging.

A. Array Chip Fabrication

A blank array chip was made by screen printing an interdigitated electrode pattern, shown in FIG. 2, onto an alumina substrate (obtained from Coors Tek, 96% alumina, 1"×0.75"×0.025"). A semi-automatic screen printer (ETP Electro-dial, Series L-400) was used. The electrode paste is available from DuPont iTechnologies, product #5715. The electrode screen that was used (obtained from Microcircuit Engineering Corporation) had an emulsion thickness of 0.5 mil. After screen printing, the parts were dried in a convection oven at 120° C. for 10 minutes and then fired. Firing was done in air using a 10 zone belt Lindberg furnace with a cycle time of 30 minutes and a peak temperature of 850° C. for 10 minutes. After the electrodes were fired onto the substrate a dielectric (DuPont iTechnologies, product #5704) pattern, shown in FIG. 2, was screen printed over the electrodes with a screen (Microcircuit Engineering Corporation), having an emulsion thickness of 0.9 mil. The parts were then dried at 120° C. for 10 minutes and fired using the same firing cycle as described above.

B. Semiconducting Metal Oxide Preparation and Application on the Array Chip

Approximately 175 mg of the semiconducting metal oxide powder or the mixture of a semiconducting metal oxide with a suitable glass frit (DuPont iTechnologies product #F2889 or F3876) or the mixture of the semiconducting metal oxide powder with other inorganic compounds was weighed out on to a glass slide with approximately 75 mg of a suitable medium (DuPont iTechnologies product #M2619) and 1 mg of a suitable surfactant (DuPont iTechnologies product #R0546). The medium and surfactant were mixed together and the metal oxide powder or mixture was added to the medium and surfactant gradually to ensure wetting. If needed, a suitable solvent (DuPont iTechnologies product #R4553) was added at this time to reduce the viscosity. The paste was then transferred to an agate mortar and pestle for more thorough mixing. Using a finely pointed wooden applicator, a very small amount of paste was then placed into one of the wells of the array chip. This procedure was repeated with each of the metal oxide powders or mixtures until all of the wells on the array chip were filled. Once the wells on the array chip were filled with pastes, the array chip was allowed to sit in a closed chamber with a low flow of $N_2$ gas passing over the chip. The array chip was then dried at 120° C. for 10 minutes. Firing was done in air using a Fisher programmable box furnace with a 1° C./minute ramp rate up to 650° C., where it was held at temperature for 30 minutes. The cooling rate was 5° C./minute to room temperature.

C. Wiring of the Array Chip

Lead wires were fabricated using approximately 1.5" of 0.005" platinum wire. One end of the wire was bare and the other end was connected to a female RS232 connector. The bare end of a platinum lead wire was attached to one of the open conductor pads on the array chip using a conducting paste (Pelco product #16023). A second lead wire was attached the same way to the other open conductor pad on the array chip. The chip was then allowed to dry for at least 4 hours at 120° C.

D. IR Thermographic Measurements

The test chamber comprised a 2.75" cube containing input and output valves for gas flow, a 1" MgF window, two thermocouple feedthroughs and two electrical feedthroughs. The electrical feedthroughs provided connections to the sample heater (Advanced Ceramics, Boralectric heater # HT-42) and the voltage/current measuring unit (Keithley Instruments model #236). The gas flows were regulated using a multi-gas controller (MKS model #647B). The sample heater was controlled using a unit from Hampton Controls (70VAC/700W phase angle). The infrared camera (Inframetrics PM390) was focused on the front surface of the array chip using a 100 µm close-up lens during the measurements.

Before the measurements were made the sample was placed inside the test chamber on top of the sample heater. The female pins on the lead wires connected to the array chip were then connected to the electrical feedthrough connected to the voltage/current measuring unit. The chamber was closed and placed in the visual path of the IR camera. Gas (100 sccm $N_2$, 25 sccm $O_2$) was then allowed to flow into the chamber during heating of the sample. Next, the sample was heated (approximately 10° C./minute) to the desired temperature and equilibrated before the voltage/current measuring unit was turned on and a voltage applied. The voltage was typically adjusted to allow a current flow of between 10–20 mA through the array.

IR thermographic images of the array of materials were taken 20 minutes after each change in the flows of the following gases: $N_2$, $O_2$, and gas mixtures as follows: 1% CO/99% $N_2$, 1% $NO_2$/99% $N_2$ and 1% $C_4H_{10}$/99% $N_2$. Unless otherwise noted, the content of all gas mixtures described below is stated in percent by volume. The temperatures of the materials in 2% $O_2$/98% $N_2$ were subtracted from their temperatures in the other gas mixtures to determine the temperature signals in the examples. ThermMonitor 95 Pro, version 1.61 (Thermoteknix Systems, Ltd.) was used to do the temperature subtractions. When exposed to a donor gas, n-type semiconducting materials will have a decrease in resistivity, increasing the current and therefore, will show an increase in temperature due to $I^2R$ heating. When exposed to an acceptor gas, n-type semiconducting materials will have an increase in resistivity, decreasing the current and therefore will show a decrease in temperature due to $I^2R$ heating. The opposite occurs with p-type semiconducting materials.

AC Impedance Samples and Measurements

A. Semiconducting Metal Oxide Paste Preparation

Approximately 2–3 grams of the semiconducting metal oxide powder or the mixture of a semiconducting metal oxide with a suitable glass frit (DuPont iTechnologies product #F2889 or F3876) or the mixture of the semiconducting metal oxide with other inorganic compounds was weighed out with an amount of a suitable medium (DuPont iTechnologies product #M2619) sufficient to provide approximately 40–70 weight % solids. These materials were then transferred to a muller (Hoover automatic muller, model #M5) where they were mixed together using a spatula until no dry powder was left. If needed, a suitable surfactant, such as DuPont iTechnologies product #R0546, was added to reduce the viscosity. Further mixing was done using the muller with 500 grams of weight for approximately 6 passes at 25 revolutions per pass. The finished pastes were then transferred to containers until needed.

B. Single Sensor Fabrication

Some of the sensing chips were prepared using a single material and not arrays of sensing materials. The single sensing sample chips were made by screen printing an interdigitated electrode pattern with electrodes, which are 0.4" long and have a 0.008" spacing onto an alumina substrate (Coors Tek, 96% alumina, 1"×1"×0.02511"). A semi-automatic screen printer (ETP Electro-dial, Series L-400) was used. The electrode paste (product #5715) is available from DuPont iTechnologies. The electrode screen (Microcircuit Engineering Corporation) had an emulsion thickness of 0.5 mil. After printing, the parts were dried in a convection oven at 120° C. for 10 minutes and then fired. Firing was done using a 10 zone belt furnace (Lindberg) with a cycle time of 30 minutes and a peak temperature of 850° C. for 10 minutes. The sensor material was then screen printed on the substrate using a screen (Microcircuit Engineering Corporation) with an open area 0.5"×0.5". This screen had an emulsion thickness of 1.0 mil. After the sensor material was printed the part was dried in a convection oven at 120° C. for 10 minutes. At this point the part was fired in air to 850° C. for 10–45 minutes using a Lindberg tube furnace.

C. Sensor Array Fabrication

A variety of electrode and sensor configurations can be used to acquire the AC impedance data of the sensor array. Described immediately below is the fabrication of a 12-material array.

The sensor array chip was made by screen printing an electrode pattern (FIG. 3) onto an alumina substrate (Coors Tek, 96% alumina, 2.5"×0.75"×0.040"). A semi-automatic screen printer (ETP Electro-dial, Series L-400) was used. The electrode paste (product #4597) is available from DuPont iTechnologies. The electrode screen (Microcircuit Engineering Corporation) had an emulsion thickness of 0.4 mil. Note in FIG. 3 that two of the sensor pads are in parallel, so that only six unique sensor material measurements can be made from this electrode configuration. After printing, the parts were dried in a convection oven at 130° C. for 10 minutes and then fired. Firing was done in air using a 10 zone belt furnace (Lindberg) with a cycle time of 30 minutes and a peak temperature of 850° C. for 10 minutes. After the electrodes were fired onto the substrate a dielectric (DuPont iTechnologies, product #QM44) pattern, shown in FIG. 3, was screen printed over the electrodes with a screen (Microcircuit Engineering Corporation), having an emulsion thickness of 1.0 mil. The parts were then dried at 130° C. for 10 minutes and fired using the same firing cycle as described above. At this point, each sensor material was screen printed on the substrate into the wells of the dielectric using the screen (Microcircuit Engineering Corporation), shown in FIG. 3. This screen had an emulsion thickness of 1.0 mil. After each sensor material was printed the part was dried in a convection oven at 130° C. for 10 minutes. After all of the sensor materials (6) were applied to this side of the sensor, the part was fired using the same firing cycle as described above. After this firing step, the above printing, drying and firing steps were repeated on the back side of the substrate to add 6 more sensor materials to the array chip.

D. AC Impedance Measurements

For single sensor material samples, a 1.2" platinum wire was connected to each of the electrodes on the samples with stainless steel screws. The ends of the platinum wires were then connected to 0.127" diameter inconel wires that run to the exterior of the test chamber. The entire lengths of the inconel wires were encased in aluminum oxide and grounded inconel tubing to eliminate interference from electromagnetic fields present in the furnace. The inconel tubes were welded into a stainless steel flange that was mounted on the end of a closed-one-end fused quartz reactor that is 4" in diameter and 24" long. The quartz reactor was wrapped with grounded stainless steel screen also to eliminate electromagnetic interference from the furnace. The entire chamber assembly was placed in the cavity of a hinged Lindberg tube furnace and the furnace was closed.

The samples were connected to the dielectric interface (Solartron 1296) and frequency response analyzer (Solartron 1260) using ten pairs of coaxial cables (one pair per sample) which ran from the inconel wires on the furnace exterior to a switch (Keithley 7001 containing two Keithley 7062 high frequency cards) and one pair of coaxial cables from the switch to the interface and analyzer. The switch, dielectric interface and frequency analyzer were all computer controlled.

The gas flows into the quartz chamber were regulated using a computer controlled system comprised of 4 independent flowmeters (MKS product #1179) and multi gas controller (MKS product #647B). The temperature of the furnace was determined using a computer controlled fuzzy logic controller (Fuji PYX).

After the samples were loaded into the furnace, the quartz reactor was purged with a synthetic air mixture during heating of the furnace. After the furnace was equilibrated at the measurement temperature, the gas concentrations ($N_2$, $O_2$, 1% CO/99% $N_2$, and 1% $NO_2$/99% $N_2$ were set to the desired values and sufficient time was allowed for the equilibration of the atmosphere in the reactor. At this point the AC impedance measurements (1 Hz to 1 MHz) from each sample were measured sequentially. Then the gas concentrations were typically set to a new value, the atmosphere was equilibrated, and another round of measurements were made. The procedure was repeated until the samples were measured in all of the desired atmospheres at a particular temperature. At this point the temperature was changed and the process repeated. After all of the measurements had been made the furnace was cooled to room temperature and the samples removed.

For the sensor array chips, a measurement system similar to that described above can be used. The only difference is that the platinum wires, which are connected to the inconel wires in the furnace, must be connected to the electrode pads on the array chip using a conducting paste (Pelco product #16023). The number of connections from the sample to the switch depends on the number of sensors on the array.

Example 1

This example shows the change in the electrical properties of 20 metal oxide semiconducting materials in the presence of 4 combustion gas compositions at 450° C. The signals listed in Table 1 below are from the infrared thermographic technique described above. The signals represent differences in temperature (° C.) of the materials when exposed to one of the 4 gas compositions shown relative to that in a comparison gas which is 2% $O_2$/98% $N_2$ and reflect the change in the electrical resistance of the semiconducting materials. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 1

| Change in temperature in ° C. | | | | | | | |
|---|---|---|---|---|---|---|---|
| | ZnO | $SnO_2$ | $NiFe_2O_4$ | $WO_3$ | 1% Nb:$TiO_2$ | $Pr_6O_{11}$ | $SrNb_2O_6$ |
| $NO_2$ in $N_2$ | −38.1 | −35.4 | −27.4 | −16.4 | −2.7 | −5.6 | −2.8 |
| $NO_2$ in 2% $O_2$/98% $N_2$ | −35.2 | −32.5 | −13.7 | −13.5 | −2.7 | — | — |
| CO in $N_2$ | 27.2 | 82 | 14 | 13.7 | — | — | 8.3 |
| $N_2$ ref. | 16.9 | 9.6 | 11.2 | 5.6 | 12.4 | — | — |
| | NiO | CuO | $Cu_2O$ | $MnTiO_3$ | $BaCuO_{2.5}$ | $AlVO_4$ | $CuMnFeO_4$ |
| $NO_2$ in $N_2$ | 5.5 | 8.2 | 8.2 | 5.6 | 6.6 | — | — |
| $NO_2$ in 2% $O_2$/98% $N_2$ | 5.5 | 5.6 | 5.5 | — | 2.6 | −2.7 | 2.6 |
| CO in $N_2$ | — | −5.5 | −13.8 | — | −2.7 | 11.3 | — |
| $N_2$ ref. | −2.8 | −5.6 | −2.8 | — | −2.7 | 8.3 | — |

TABLE 1-continued

| | Change in temperature in ° C. | | | | | |
|---|---|---|---|---|---|---|
| | $LaFeO_3$ | $CuGaO_2$ | $CuFe_2O_4$ | $Zn_4TiO_6$ | $La_2CuO_4$ | $SrCu_2O_2$ |
| $NO_2$ in $N_2$ | — | -2.8 | -5.5 | -5.7 | 4.2 | — |
| $NO_2$ in 2% $O_2$/98% $N_2$ | — | — | -2.5 | — | — | 2.6 |
| CO in $N_2$ | -2.8 | — | — | 7.3 | — | — |
| $N_2$ ref. | — | — | — | — | — | — |

The following measurements were done with other than 10 V. $Pr_6O_{11}$ was measured using 1 V; $BaCuO_{2.5}$, $CuMnFeO_4$, $CuGaO_2$ and $CuFe_2O4$ were measured using 16 V; $Zn_4TiO_6$ was measured using 20 V; $LaCuO_4$ and $SrCu_2O_2$ were measured using 12 V.

Example 2

This example shows the change in the electrical properties of 8 metal oxide semiconducting materials in the presence of 5 combustion gas compositions at 450° C. The signals listed in Table 2 below are from the infrared thermographic technique. The signals are differences in temperature (° C.) of the semiconducting materials when exposed to the gas compositions shown relative to that in a comparison gas which is 2% $O_2$/98% $N_2$. All of the signals were generated with 10 V across the semiconducting materials, unless otherwise specified. Blank spaces indicate that there was no detectable signal when that gas composition was contacted with that material. Unless otherwise specified, the gases were measured at 2000 ppm in $N_2$.

TABLE 2

| | Change in temperature in ° C. | | | | | | | |
|---|---|---|---|---|---|---|---|---|
| | ZnO | $SnO_2$ | $WO_3$ | $SrNb_2O_6$ | NiO | CuO | $Cu_2O$ | $AlVO_4$ |
| $NO_2$ in $N_2$ | -38.1 | -35.4 | -16.4 | -2.8 | 5.5 | 8.2 | 8.2 | — |
| $NO_2$ in 2% $O_2$/98% $N_2$ | -35.2 | -32.5 | -13.5 | — | 5.5 | 5.6 | 5.5 | -2.7 |
| CO in $N_2$ | 27.2 | 8.2 | 13.7 | 8.3 | | -5.5 | -13.8 | 11.3 |
| $N_2$ ref. | 16.9 | 9.6 | 5.6 | — | -2.8 | -5.6 | -2.8 | 8.3 |
| 1% $C_4H_{10}$/99% $N_2$ | 38 | 28 | 22 | | -6 | -7 | -11 | 11 |

Example 3

This example shows the change in the electrical properties of 26 metal oxide semiconducting materials in the presence of 4 combustion gas compositions at 600° C. The signals listed in Table 3 immediately below were obtained using an infrared thermographic technique. The signals are measurements of the differences in temperature (° C.) of the materials when exposed to the gas compositions shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 3

| | Change in temperature in ° C. | | | | | | | |
|---|---|---|---|---|---|---|---|---|
| | ZnO | $SnO_2$ | $NiFe_2O_4$ | 1% $Nb:TiO_2$ | $WO_3$ | $FeTiO_3$ | $SrTiO_3$ | NiO |
| $NO_2$ in $N_2$ | -54.4 | -48.3 | -36.3 | -24.2 | -18.1 | -6.1 | 3 | 6 |
| $NO_2$ in 2% $O_2$/98% $N_2$ | -48.3 | -48.3 | -30.2 | -12.1 | -18.1 | -6.1 | 6 | 6 |
| CO in $N_2$ | 28.5 | 18.1 | 18.5 | 42.3 | 24.1 | — | — | -6 |
| $N_2$ | 30.2 | 24.1 | 15.1 | 24.1 | 6 | 3 | — | -9.1 |

TABLE 3-continued

Change in temperature in ° C.

| | AlVO$_4$ | CuO | Cu$_2$O | LaFeO$_3$ | BaCuO$_{2.5}$ | Fe$_2$O$_3$ | SrNb$_2$O$_6$ | ZnO + 2.5% F2889 |
|---|---|---|---|---|---|---|---|---|
| NO$_2$ in N$_2$ | — | — | — | — | — | — | — | -24 |
| NO$_2$ in 2% O$_2$/98% N$_2$ | -6.1 | 6 | 6 | — | — | — | — | -18 |
| CO in N$_2$ | 18.1 | -6 | -12.1 | -3 | -6 | 72.5 | 28.5 | 18 |
| N$_2$ | 18.1 | -3 | — | — | -6 | — | 18.1 | 21 |

| | ZnO + 10% F3876 | SnO$_2$ + 5% F2889 | WO$_3$ + 10% F3876 | CuFe$_2$O$_4$ | Zn$_4$TiO$_6$ | ZnTiO$_3$ | Tm$_2$O$_3$ | Yb$_2$O$_3$ | Fe:ZrO$_2$ | MnCrO$_3$ |
|---|---|---|---|---|---|---|---|---|---|---|
| NO$_2$ in N$_2$ | -42 | -6 | -15 | -6 | -12 | -6 | -6 | -6 | -6 | — |
| NO$_2$ in 2% O$_2$/98% N$_2$ | -24 | -6 | -18 | -6 | — | — | — | — | — | — |
| CO in N$_2$ | 12 | 24 | 6 | — | 6 | — | — | — | 6 | 24 |
| N$_2$ | 27 | 9 | 18 | — | 6 | — | — | — | — | — |

All of the measurements were obtained using 10 V, except that BaCuO$_{2.5}$ was measured with 4 V; Fe$_2$O$_3$ was measured with 1 V; ZnO+2.5% F2889, ZnO+10% F3876, SnO$_2$+5% F2889, Tm$_2$O$_3$, Yb$_2$O$_3$, Fe:ZrO$_2$ and MnCrO$_3$ were measured with 5 V; WO$_3$+10% F3876 was measured with 2 V; CuFe$_2$O$_4$ was measured with 6 V; and Zn$_4$TiO$_6$ and ZnTiO$_3$ were measured using 20 V.

Example 4

This example illustrates that a set of 4 metal oxide materials of Example 3 could be used to differentiate the 4 gas compositions shown at 600° C. using the IR thermographic signals. The results are shown in Table 4 below. The signals are measurements of the differences in temperature (° C.) of the materials when exposed to the gases shown relative to that in a comparison gas which is 2% O$_2$/98% N$_2$. All of the signals were generated with 10 V across the materials, unless otherwise specified. Blank spaces indicate that there was no detectable signal when that gas composition was contacted with that material. Unless otherwise specified, the gases were measured at 2000 ppm in N$_2$.

TABLE 4

Change in temperature in ° C.

| | SrTiO$_3$ | Cu$_2$O | Fe$_2$O$_3$ | SrNb$_2$O$_6$ |
|---|---|---|---|---|
| NO$_2$ in N$_2$ | 3 | — | — | — |
| NO$_2$ in 2% O$_2$/98% N$_2$ | 6 | 6 | — | — |
| CO in N$_2$ | — | -12.1 | 72.5 | 28.5 |
| N$_2$ | — | — | — | 18.1 |

Example 5

This example demonstrates that this second set of 4 metal oxide materials of Example 3 could be used to differentiate the 4 gas compositions shown at 600° C. using the IR thermographic signals. The results are shown in Table 5 below. The signals are measurements of the differences in temperature (° C.) of the materials when exposed to the gases shown relative to that in a comparison gas which is 2% O$_2$/98% N$_2$. All of the signals were generated with 10 V across the materials, unless otherwise specified. Blank spaces indicate that there was no detectable signal when that gas composition was contacted with that material. Unless otherwise specified, the gases were measured at 2000 ppm in N$_2$.

TABLE 5

Change in temperature in ° C.

| | ZnO | AlVO$_4$ | LaFeO$_3$ | BaCuO$_{2.5}$ |
|---|---|---|---|---|
| NO$_2$ in N$_2$ | -54.4 | — | — | — |
| NO$_2$ in 2% O$_2$/98% N$_2$ | -48.3 | -6.1 | — | — |
| CO in N$_2$ | 28.5 | 18.1 | -3 | -6 |
| N$_2$ | 30.2 | 18.1 | — | -6 |

Comparative Example A

This comparative example demonstrates that this set of 6 materials of Example 3 can not be used to differentiate the 2 gas compositions at 600° C. using the IR thermographic signals, and illustrates the importance of the proper selection of materials. The results are shown in Table 5A below. The signals are measurements of the differences in temperature (° C.) of the materials when exposed to the gas compositions shown relative to that in a comparison gas which is 2% O$_2$/98% N$_2$. All of the signals were generated with 10 V across the materials, unless otherwise specified. Blank spaces indicate that there was no detectable signal when that gas composition was contacted with that material. Unless otherwise specified, the gases were measured at 2000 ppm in N$_2$.

TABLE 5a

Change in temperature in ° C.

| | SnO$_2$ | WO$_3$ | FeTiO$_3$ | NiO | SnO$_2$ + 5% F2889 | CuFe$_2$O$_4$ |
|---|---|---|---|---|---|---|
| NO$_2$ in N$_2$ | -48.3 | -18.1 | -6.1 | 6 | -6 | -6 |
| NO$_2$ in 2% O$_2$/98% N$_2$ | -48.3 | -18.1 | -6.1 | 6 | -6 | -6 |

Comparative Example B

This comparative example demonstrates that this set of 3 materials can not be used to differentiate the 2 gas compositions at 600° C. using the IR thermographic signals, and illustrates the importance of the proper selection of materials. The results are shown in Table 5B below. The signals are measurements of the differences in temperature (° C.) of the materials when exposed to the gas compositions shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 5b

| | Change in temperature in ° C. | | |
|---|---|---|---|
| | $AlVO_4$ | $BaCuO_{2.5}$ | $Zn_4TiO_6$ |
| CO in $N_2$ | 18.1 | −6 | 6 |
| $N_2$ | 18.1 | −6 | 6 |

Example 6

This example illustrates the use of the AC impedance technique for the measurement of the response of 19 metal oxide semiconducting materials in the presence of 4 gas compositions at 400° C. The signals listed in Table 6 below are the ratios of the magnitudes of the impedances of the materials when exposed to the gas compositions shown to the magnitudes of the impedances in 10,000 ppm $O_2$ in $N_2$. The gases used were 200 ppm $NO_2$ in $N_2$, 200 ppm $NO_2$ and 10,000 ppm $O_2$ in $N_2$, 1000 ppm CO in $N_2$, and $N_2$.

TABLE 6

| | $MgAl_2O_4$ | 1% Zn:$MgAl_2O_4$ | ZnO | $WO_3$ | $NiFe_2O_4$ | $SnO_2$ | $TiO_2$ |
|---|---|---|---|---|---|---|---|
| $NO_2$ in $N_2$ | 0.6245 | 0.5544 | 55.85 | 8.772 | 5.008 | 9.243 | 1.536 |
| $NO_2$ in $O_2$/$N_2$ | 0.7680 | 0.6787 | 47.38 | 9.468 | 12.93 | 10.56 | 1.585 |
| CO in $N_2$ | 1.531 | 1.459 | 0.1235 | 0.1865 | 1.248 | 0.0051 | 0.0116 |
| $N_2$ | 0.8242 | 0.9219 | 4.1290 | 1.716 | 1.327 | 0.3208 | 1.055 |

| | $MnTiO_3$ | NiO | $SrNb_2O_6$ | $CeVO_4$ | 1% Nb:$TiO_2$ | $FeTiO_3$ | $Pr_6O_{11}$ |
|---|---|---|---|---|---|---|---|
| $NO_2$ in $N_2$ | 0.8643 | 0.5692 | 1.217 | 0.9847 | 1.937 | 1.299 | 0.5475 |
| $NO_2$ in $O_2$/$N_2$ | 0.8475 | 0.9662 | 1.228 | 0.9977 | 1.674 | 1.034 | 0.5452 |
| CO in $N_2$ | 37.35 | 9.679 | 0.6501 | 1.045 | 0.0112 | 0.6009 | 1.184 |
| $N_2$ | 1.264 | 1.257 | 1.011 | 1.001 | 0.8811 | 1.028 | 1.103 |

| | $SrTiO_3$ | $Ba_2Cu_2O_5$ | $CuMnFe_2O_4$ | $LaFeO_3$ | $Zn_2V_2O_7$ |
|---|---|---|---|---|---|
| $NO_2$ in $N_2$ | 0.6524 | 0.7869 | 0.9559 | 0.8401 | 1.209 |
| $NO_2$ in $O_2$/$N_2$ | 0.7596 | 0.7834 | 0.9399 | 0.8506 | 1.114 |
| CO in $N_2$ | 0.0178 | 0.7603 | 0.6089 | 2037 | 0.8529 |
| $N_2$ | 1.061 | 1.063 | 1.136 | 1.756 | 0.9900 |

Example 7

This example illustrates the use of the AC impedance technique for the measurement of the response of 19 metal oxide semiconducting materials in the presence of 4 gas compositions at 550° C. The signals listed in the table are from the AC impedance technique. The signals are the ratios of the magnitudes of the impedances of the materials when exposed to the gas compositions shown to the magnitudes of the impedances in 10,000 ppm $O_2$ in $N_2$. The gases used were 200 ppm $NO_2$ in $N_2$, 200 ppm $NO_2$ & 10,000 ppm $O_2$ in $N_2$, 1000 ppm CO in $N_2$, and $N_2$.

TABLE 7

| | $MgAl_2O_4$ | 1% Zn:$MgAl_2O_4$ | ZnO | $WO_3$ | $NiFe_2O_4$ | $SnO_2$ |
|---|---|---|---|---|---|---|
| $NO_2$ in $N_2$ | 0.9894 | 0.9583 | 3.866 | 2.335 | 3.025 | 1.655 |
| $NO_2$ in $O_2$/$N_2$ | 0.8937 | 0.8984 | 5.272 | 2.006 | 3.553 | 3.390 |
| CO in $N_2$ | 1.046 | 0.9697 | 0.0133 | 0.2034 | 0.2506 | 0.0069 |
| $N_2$ | 1.067 | 1.060 | 0.7285 | 0.9526 | 1.208 | 0.2666 |

TABLE 7-continued

|  | $TiO_2$ | $MnTiO_3$ | NiO | $SrNb_2O_6$ | $CeVO_4$ | 1% $Nb:TiO_2$ | $FeTiO_3$ |
|---|---|---|---|---|---|---|---|
| $NO_2$ in $N_2$ | 1.135 | 1.010 | 0.9483 | 1.006 | 1.003 | 1.271 | 1.193 |
| $NO_2$ in $O_2/N_2$ | 1.314 | 1.014 | 0.5207 | 1.044 | 0.9975 | 1.302 | 1.073 |
| CO in $N_2$ | 0.0017 | 44.00 | 1.194 | 0.2814 | 1.104 | 0.0021 | 0.6743 |
| $N_2$ | 0.7263 | 1.280 | 1.341 | 0.9830 | 1.024 | 0.477 | 1.054 |

|  | $Pr_6O_{11}$ | $SrTiO_3$ | $Ba_2Cu_2O_5$ | $CuMnFe_2O_4$ | $LaFeO_3$ | $Zn_2V_2O_7$ |
|---|---|---|---|---|---|---|
| $NO_2$ in $N_2$ | 1.223 | 0.9055 | 0.7071 | 1.148 | 1.302 | 1.199 |
| $NO_2$ in $O_2/N_2$ | 0.9656 | 0.9881 | 0.3812 | 0.9891 | 0.9429 | 1.086 |
| CO in $N_2$ | 62.76 | 0.0029 | 3.0892 | 2.557 | 123.3 | 0.4726 |
| $N_2$ | 1.495 | 1.210 | 1.333 | 1.681 | 1.789 | 0.9034 |

Example 8

This example illustrates the use of the AC impedance technique for the measurement of the response of 23 semiconducting materials in the presence of 4 gas compositions at 650–700° C. The signals listed in the table are from the AC impedance technique. The signals are the ratios of the magnitudes of the impedances of the materials when exposed to the gas compositions shown to the magnitudes of the impedances in 10,000 ppm $O_2$ in $N_2$. The gases used were 200 ppm $NO_2$ in $N_2$, 200 ppm $NO_2$ & 10,000 ppm $O_2$ in $N_2$, 1000 ppm CO in $N_2$, and $N_2$.

TABLE 8

|  | $MgAl_2O_4$ | 1% $Zn:MgAl_2O_4$ | ZnO | $WO_3$ | $NiFe_2O_4$ | $SnO_2$ | $TiO_2$ |
|---|---|---|---|---|---|---|---|
| $NO_2$ in $N_2$ | 0.9450 | 1.022 | 0.4876 | 0.7151 | 0.5807 | 0.5419 | 0.5617 |
| $NO_2$ in $O_2/N_2$ | 0.6412 | 0.8310 | 1.235 | 1.281 | 1.105 | 0.8265 | 1.030 |
| CO in $N_2$ | 0.9074 | 0.9684 | 0.0348 | 0.2693 | 0.0408 | 0.0238 | 0.0015 |
| $N_2$ | 1.056 | 1.100 | 0.2753 | 0.6332 | 0.4421 | 0.3521 | 0.3957 |

|  | $MnTiO_3$ | NiO | $SrNb_2O_6$ | $CeVO_4$ | 1% $Nb:TiO_2$ | $FeTiO_3$ | $Pr_6O_{11}$ |
|---|---|---|---|---|---|---|---|
| $NO_2$ in $N_2$ | 1.445 | 1.379 | 0.8852 | 1.050 | 0.5711 | 0.9072 | 1.516 |
| $NO_2$ in $O_2/N_2$ | 0.9561 | 0.8127 | 0.9862 | 1.135 | 0.8263 | 0.9524 | 0.9814 |
| CO in $N_2$ | 113.3 | 1.782 | 0.0301 | 1.565 | 0.0035 | 0.4346 | 8005 |
| $N_2$ | 1.877 | 1.409 | 0.8788 | 1.080 | 0.2802 | 0.8050 | 1.962 |

|  | $SrTiO_3$ | $Ba_2Cu_2O_5$ | $CuMnFe_2O_4$ | $LaFeO_3$ | $Zn_2V_2O_7$ |
|---|---|---|---|---|---|
| $NO_2$ in $N_2$ | 1.051 | 0.5615 | 3.401 | 1.331 | 0.8631 |
| $NO_2$ in $O_2/N_2$ | 0.9320 | 0.9703 | 1.001 | 1.013 | 0.9459 |
| CO in $N_2$ | 0.0020 | 381.3 | 2.198 | 43.11 | 0.4672 |
| $N_2$ | 1.076 | 1.308 | 4.250 | 1.673 | 0.6574 |

|  | ZnO + 2.5% F2889 | ZnO + 10% F3876 | $SnO_2$ + 5% F2889 | $WO_3$ + 10% F3876 |
|---|---|---|---|---|
| $NO_2$ in $N_2$ | 0.5810 | 0.7944 | 0.6270 | 0.6055 |
| $NO_2$ in $O_2/N_2$ | 1.141 | 1.176 | 0.8927 | 1.284 |
| CO in $N_2$ | 0.0020 | 0.0016 | 0.0043 | 0.0122 |
| $N_2$ | 0.1054 | 0.1338 | 0.2780 | 0.4862 |

Example 9

This example illustrates the use of the AC impedance technique for the measurement of the response of 16 semiconducting materials in the presence of 4 gas compositions at 800° C. The signals listed in the table are from the AC impedance technique. The signals are the ratios of the magnitudes of the impedances of the materials when exposed to the gas compositions shown to the magnitudes of the impedances in 10,000 ppm $O_2$ in $N_2$. The gases used were 200 ppm $NO_2$ in $N_2$, 200 ppm $NO_2$ & 10,000 ppm $O_2$ in $N_2$, 1000 ppm CO in $N_2$, and $N_2$.

TABLE 9

|  | ZnO | WO$_3$ | NiFe$_2$O$_4$ | SnO$_2$ | TiO$_2$ | MnTiO$_3$ | NiO | SrNb$_2$O$_6$ |
|---|---|---|---|---|---|---|---|---|
| NO$_2$ in N$_2$ | 0.3980 | 0.5737 | 0.6710 | 0.4050 | 0.4859 | 1.981 | 1.917 | 0.7555 |
| NO$_2$ in O$_2$/N$_2$ | 1.594 | 1.117 | 4.795 | 6.456 | 1.052 | 1.497 | 0.8529 | 0.9928 |
| CO in N$_2$ | 0.688 | 0.2610 | 0.0642 | 0.2349 | 0.0014 | 123.2 | 5.129 | 0.0144 |
| N$_2$ | 0.3070 | 0.5103 | 0.5339 | 0.2852 | 0.3093 | 2.882 | 2.124 | 0.5167 |
|  | CeVO$_4$ | 1% Nb:TiO$_2$ | FeTiO$_3$ | Pr$_6$O$_{11}$ | SrTiO$_3$ | Ba$_2$Cu$_2$O$_5$ | CuMnFe$_2$O$_4$ | LaFeO$_3$ |
| NO$_2$ in N$_2$ | 1.013 | 0.3280 | 0.6799 | 1.569 | 0.0049 | 4.061 | 2.869 | 1.252 |
| NO$_2$ in O$_2$/N$_2$ | 1.058 | 1.006 | 0.9982 | 1.010 | 0.0260 | 0.9811 | 0.9389 | 1.326 |
| CO in N$_2$ | 2.165 | 0.0047 | 0.2831 | 3530 | 1.004 | 216.0 | 0.8810 | 63.36 |
| N$_2$ | 1.075 | 0.1960 | 0.5600 | 2.999 | 1.048 | 7.445 | 3.413 | 1.612 |

What is claimed is:

1. A method for calculating the concentration of at least two individual analyte gas components in a multi-component gas mixture having a temperature of about 400° C. or more, comprising:
    (a) providing within the gas mixture an array of at least three chemo/electro-active materials, each chemo/electro-active material having a different electrical response characteristic upon exposure to each of the individual analyte gas components than each of the other chemo/electro-active materials, wherein at least one chemo/electro-active material, when at a temperature of about 400° C. or more,
        (i) has an electrical resistivity in the range of about 1 ohm-cm to about $10^5$ ohm-cm, and
        (ii) exhibits a change in electrical resistance of at least about 0.1 percent upon exposure of the material to an analyte gas component, as compared to the resistance before exposure;
    (b) heating the array to a temperature above 500° C.;
    (c) determining an electrical response of each chemo/electro-active material upon exposure of the array to the unseparated components of the gas mixture;
    (d) inputting the electrical responses of the chemo/electro-active materials, but not a baseline response value, a comparison response value or a reference gas value, to a pattern recognition technique; and
    (e) calculating the concentration of each of the individual analyte gas components from the inputs in step (d).

2. A method according to claim 1 wherein the gas mixture is an emission from a combustion process.

3. A method according to claim 1 wherein the electrical response characteristic of each material upon exposure to the gas mixture at a selected temperature is quantifiable as a value, and the response value of at least one material is constant or varies by no more than about twenty percent during exposure of the material to an analyte gas component at the selected temperature for a period of at least about one minute.

4. A method according to claim 1 wherein the electrical response is selected from the group consisting of resistance, impedance, capacitance, voltage or current.

5. A method according to claim 1 wherein the gas mixture comprises one or more members of the group consisting of oxygen, carbon monoxide, a nitrogen oxide, a hydrocarbon, CO$_2$, H$_2$S, sulfur dioxide, a halogen, hydrogen, water vapor, ammonia, alcohol, a solvent vapor, an ether, a ketone, an aldehyde, a carbonyl, and a microorganism.

6. A method according to claim 1 wherein the gas mixture comprises one or more members of the group consisting of oxygen, a nitrogen oxide, a hydrocarbon, and ammonia.

7. A method according to claim 1 wherein the gas mixture comprises one or more members of the group consisting of a nitrogen oxide and ammonia.

8. A method according to claim 1 wherein the gas mixture comprises one or more members of the group consisting of oxygen and a hydrocarbon.

9. A method according to claim 1 wherein the gas mixture is provided from a manufacturing process, a waste stream, environmental monitoring, or a medical, agricultural, food or beverage operation.

10. A method according to claim 1 wherein at least one chemo/electro-active material is a metal oxide.

11. A method according to claim 10 wherein the chemo/electro-active materials comprise one or more members of the group consisting of $M^1O_x$, $M^1_aM^2_bO_x$, and $M^1_aM^2_bM^3_cO_x$ wherein
    $M^1$, $M^2$ and $M^3$ are metals that form stable oxides when fired in the presence of oxygen above 500° C.;
    $M^1$ is selected from Periodic Groups 2–15 and the lanthanide group;
    $M^2$ and $M^3$ are independently selected from Periodic Groups 1–15 and the lanthanide group;
    a, b, and c are each independently in the range of about 0.0005 to about 1, provided that a+b+c=1; and
    x is a number sufficient so that the oxygen present balances the charges of the other elements in the compound.

12. A method according to claim 10 wherein the chemo/electro-active materials comprise one or more members of the group consisting of $M^1O_x$, $M^1_aM^2_bO_x$, and $M^1_aM^2_bM^3_cO_x$ wherein
    $M^1$ is selected from the group consisting of Ce, Co, Cu, Fe, Ga, Nb, Ni, Pr, Ru, Sn, Ti, Tm, W, Yb, Zn, and Zr;
    $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same m $M^1_aM^2_bM^3_cO_x$;
    a, b, and c are each independently in the range of about 0.0005 to about 1, provided that a+b+c=1; and
    x is a number sufficient so that the oxygen present balances the charges of the other elements in the compound.

13. A method according to claim 10 wherein the chemo/electro-active materials comprise one or more members of the group consisting of $M^1O_x$, $M^1_aM^2_bO_x$, and $M^1_aM^2_bM^3_cO_x$ wherein
    $M^1O_x$ is selected from the group consisting of Ce$_a$O$_x$, CoO$_x$, CuO$_x$, FeO$_x$, GaO$_x$, NbO$_x$, NiO$_x$, PrO$_x$, RuO$_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;

$M^1{}_aM^2{}_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZn_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with fit additive, $Ni_aZr_bO_x$ with frit additive, or $Ta_aTi_bO_x$ with frit additive; and $M^1{}_aM^2{}_bM^3{}_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bWcO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$;

a, b, and c are each independently in the range of about 0.0005 to about 1, provided that a+b+c=1; and x is a number sufficient so that the oxygen present balances the charges of the other elements in the compound.

14. A method according to claim 10 wherein the chemo/electro-active materials comprise first and second chemo/electro-active materials selected from the pairings in the group consisting of (i) the first material is $M^1O_x$, and the second material is $M^1{}_aM^2{}_bO_x$;

(ii) the first material is $M^1O_x$, and the second material is $M^1{}_aM^2{}_bM^3{}_cO_x$;

(iii) the first material is $M^1{}_aM^2{}_bO_x$, and the second material is $M^1{}_aM^2{}_bM^3{}_cO_x$;

(iv) the first material is a first $M^1O_x$, and the second material is a second $M^1O_x$;

(v) the first material is a first $M^1{}_aM^2{}_bO_x$, and the second material is a second $M^1{}_aM^2{}_bO_x$; and (vi) the first material is a first $M^1{}_aM^2{}_bM^3{}_cO_x$, and the second material is a second $M^1{}_aM^2{}_bM^3{}_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$;

a, b and c are each independently about 0.0005 to about 1, provided that a+b+c=1; and x is a number sufficient so that the oxygen present balances the charges of the other elements in the compound.

15. A method for analyzing at least one individual gas component in a multi-component gas mixture, comprising:

(a) providing an array of at least two chemo/electro-active materials, each chemo/electro-active material having a different electrical response characteristic upon exposure at a selected temperature to the individual gas component than each of the other chemo/electro-active materials, the electrical response characteristic of each material being quantifiable as a value, wherein the response value of at least one material is constant or varies by no more than about twenty percent during exposure of the material to an individual gas component at the selected temperature for a period of at least about one minute;

(b) heating the array to a temperature above 500° C.;

(c) determining the electrical response value of each chemo/electro-active material upon exposure of the array to the gas mixture;

(d) inputting the electrical responses of the chemo/electro-active materials, but not a baseline response value, a comparison response value or a reference gas value, to a pattern recognition technique; and (e) performing an analysis of the individual gas component from the inputs in step (d).

16. A method according to claim 15 wherein the array is situated within the gas mixture, which has a temperature of about 400° C. or more.

17. A method according to claim 15 wherein the gas mixture is an emission from a combustion process.

18. A method according to claim 15 wherein the analysis performed comprises calculating the concentration within the gas mixture of the individual gas component.

19. A method according to claim 15 wherein the array is situated in the gas mixture, which has a temperature of less than about 400° C., and the array has a substantially constant temperature above 500° C.

20. A method according to claim 15 wherein the component gases in the mixture are not separated.

21. A method according to claim 15 wherein at least one chemo/electro-active material, when at a temperature of about 400° C. or more, (i) has an electrical resistivity in the range of about 1 ohm-cm to about $10^5$ ohm-cm, and (ii) exhibits a change in electrical resistance of at least about 0.1 percent upon exposure of the material to an analyte gas component, as compared to the resistance before exposure.

22. A method according to claim 15 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

23. A method according to claim 15 wherein the gas mixture comprises one or more members of the group consisting of oxygen, a nitrpgen oxide, a hydrocarbon, and ammonia.

24. A method according to claim 15 wherein the gas mixture comprises one or more members of the group consisting of a nitrogen oxide and ammonia.

25. A method according to claim 15 wherein the gas mixture comprises one or more members of the group consisting of oxygen and a hydrocarbon.

26. A method according to claim 15 wherein the gas mixture is provided from a manufacturing process, a waste stream, environmental monitoring, or a medical, agricultural, food or beverage operation.

27. A method according to claim 15 lwherein at least one chemo/electro-active material is a metal oxide.

28. A method according to claim 27 wherein the chemo/electro-active materials comprise one or more members of the group consisting of $M^1O_x$, $M^1_aM^2_bO_x$, and $M^1_aM^2_bM^3_cO_x$ wherein $M^1$, $M^2$ and $M^3$ are metals that form stable oxides when fired in the presence of oxygen above 500° C.;

$M^1$ is selected from Periodic Groups 2–15 and the lanthanide group;

$M^2$ and $M^3$ are independently selected from Periodic Groups 1–15 and the larithanide group;

a, b, and c are each independently in the range of about 0.0005 to about 1, provided that a+b+c=1; and x is a number sufficient so that the oxygen present balances the charges of the other elements in the compound.

29. A method according to claim 27 wherein the chemo/electro-active materials comprise one or more members of the group consisting of $M^1O_x$, $M^1_aM^2_bO_x$, and $M^1_aM^2_bM^3_cO_x$ wherein $M^1$ is selected from the group consisting of Ce, Go, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;

a, b, and c are each independently in the range of about 0.0005 to about 1, provided that a+b+c=1; and x is a number sufficient so that the oxygen present balances the charges of the other elements in the compound.

30. A method according to claim 27 wherein the chemo/electro-active materials comprise one or more members of the group consisting of $M^1O_x$, $M^1_aM^2_bO_x$, and $M^1_aM^2_bM^3_cO_x$ wherein $M^1O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;

$M^1_aM^2_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $VaZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aNi_bO_x$ with frit additive, $Fe_aTi_bO_x$ with fit additive, $Nb_aTi_bO_x$ with frit additive, $Nb_aW_bO_x$ with frit additive, $Ni_aZn_bO_x$ with frit additive, $Ni_aZr_bO_x$ with frit additive, or $Ta_aTi_bO_x$ with frit additive; and $M^1_aM^2_bM^3_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$;

a, b, and c are each independently in the range of about 0.0005 to about 1, provided that a+b+c=1; and x is a number sufficient so that the oxygen present balances the charges of the other elements in the compound.

31. A method according to claim 27 wherein the chemo/electro-active materials comprise first and second chemo/electro-active materials selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same m $M^1_aM^2_bM^3_cO_x$;

a, b and c are each independently about 0.0005 to about 1, provided that a+b+c=1; and x is a number sufficient so that the oxygen present balances the charges of the other elements in the compound.

32. A method according to claim 15 wherein the electrical response is selected from the group consisting of resistance, nnpedance, capacitance, voltage or current.

33. A method for directly sensing gas components in a multi-component gas system, comprising
   (a) exposing a chemical sensor comprising an array of at least two chemo/electro-active materials to a multi-component gas system;
   (b) heating the array to a temperature above 500° C.;
   (c) detecting a response;
   (d) directly measuring the response of each chemo/electro-active material;
   (e) inputting the electrical responses of the chemo/electro-active materials, but not a baseline response value, a cornparison response value or a reference gas value, to a pattern recognition technique; and
   (f) detecting the presence of and/or calculating the concentration of one or more individual analyte gas components in the system from the inputs in step (e).

34. A method according to claim 33 wherein at least one chemo/electro-active material, when at a temperature of about 400° C. or more, (i) has an electrical resistivity in the range of about 1 ohm-cm to about $10^5$ ohm-cm, and (ii) exhibits a change in electrical resistance of at least about 0.1 percent upon exposure of the material to an individual gas component, as compared to the resistance before exposure.

35. A method according to claim 33 wherein the electrical response characteristic of each material upon exposure to the gas mixture at a selected temperature is quantifiable as a value, and the response value of at least one material is constant or varies by no more than about twenty percent during exposure of the material to an analyte gas component at the selected temperature for a period of at least about one minute.

36. A method according to claim 33 wherein the electrical response is selected from the group consisting of resistance, impedance, capacitance, voltage or current.

37. A method according to claim 33 wherein the array is situated within the gas mixture, which has a temperature of about 400° C. or more.

38. A method according to claim 33 wherein the array is situated in the gas mixture, which has a temperature of less than about 400° C., and the array has a substantially constant temperature above 500° C.

39. A method according to claim 33 wherein the component gases in the gas mixture are not separated.

40. A method according to claim 33 wherein the analysis performed comprises calculating the concentration within the gas mixture of the individual gas component.

41. A method according to claim 33 wherein gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

42. A method according to claim 33 wherein the gas mixture comprises one or more members of the group consisting of oxygen, a nitrogen oxide, a hydrocarbon, and ammonia.

43. A method according to claim 33 wherein the gas mixture comprises one or more members of the group consisting of a nitrogen oxide and ammonia.

44. A method according to claim 33 wherein the gas mixture comprises one or more members of the group consisting of oxygen and a hydrocarbon.

45. A method according to claim 33 wherein the gas mixture is an emission from a combustion process.

46. A method according to claim 33 wherein the gas mixture is provided from a manufacturing process, a waste stream, environmental monitoring, or a medical, agricultural, food or beverage operation.

47. A method according to claim 33 wherein at least one chemo/electro-active material is a metal oxide.

48. A method according to claim 47 wherein the chemo/electro-active materials comprise one or more members of the group consisting of $M^1O_x$, $M^1_aM^2_bO_x$, and $M^1_aM^2_bM^3_cO_x$ wherein
   $M^1$, $M^2$ and $M^3$ are metals that form stable oxides when fired in the presence of oxygen above 500° C.;
   $M^1$ is selected from Periodic Groups 2–15 and the lanthanide group;
   $M^2$ and $M^3$ are independently selected from Periodic Groups 1–15 and the lanthanide group;
   a, b, and c are each independently in the range of about 0.0005 to about 1, provided that a+b+c=1; and
   x is a number sufficient so that the oxygen present balances the charges of the other elements in the compound.

49. A method according to claim 47 wherein the chemo/electro-active materials comprise one or more members of the group consisting of $M^1O_x$, $M^1_aM^2_bO_x$, and $M^1_aM^2_bM^3_cO_x$ wherein
   $M^1$ is selected from the group consisting of Ce, Co, Cu, Fe, Ga, Nb, Ni, Pr, Ru, Sn, Ti, Tm, W, Yb, Zn, and Zr;
   $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;
   a, b, and c are each independently in the range of about 0.0005 to about 1, provided that a+b+c=1; and
   x is a number sufficient so that the oxygen present balances the charges of the other elements in the compound.

50. A method according to claim 47 wherein the chemo/electro-active materials comprise one or more members of the group consisting of $M^1O_x$, $M^1_aM^2_bO_x$, and $M^1_aM^2_bM^3_cO_x$ wherein
   $M^1O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;
   $M^1_aM^2_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, or $Ta_aTi_bO_x$ with frit additive; and $M^1_aM^2_bM^3_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_aO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$;

a, b, and c are each independently in the range of about 0.0005 to about 1, provided that a+b+c=1; and x is a number sufficient so that the oxygen present balances the charges of the other elements in the compound.

51. A method according to claim 47 wherein the chemo/electro-active materials comprise first and second chemo/electro-active materials selected from the pairings in the group consisting of (i) the first material is $M^1O_x$, and the second material is $M^1_aM^2_bO_x$;

(ii) the first material is $M^1_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;

a, b and c are each independently about 0.0005 to about 1, provided that a+b+c1; and x is a number sufficient so that the oxygen present balances the charges of the other elements in the compound.

52. A method for directly sensing gas components in a multi-component gas system, comprising (a) exposing a chemical sensor comprising an array of at least two chemo/electro-active materials to a multi-component gas system;

(b) heating the array to a temperature above 500° C.;

(c) detecting a response;

(d) directly measuring the response of each chemo/electro-active material;

(e) inputting only the electrical responses of the chemo/electro-active materials to a pattern recognition technique; and (f) detecting the presence of and/or calculating the concentration of one or more individual analyte gas components in the system from the inputs in step (e).

53. A method according to claim 52 wherein at least one chemo/electro-active material, when at a temperature of about 400° C. or more, (i) has an electrical resistivity in the range of about 1 ohm-cm to about $10^5$ ohm-cm, and (ii) exhibits a change in electrical resistance of at least about 0.1 percent upon exposure of the material to an individual gas component, as compared to the resistance before exposure.

54. A method according to claim 52 wherein the electrical response characteristic of each material upon exposure to the gas mixture at a selected temperature is quantifiable as a value, and the response value of at least one material is constant or varies by no more than about twenty percent during exposure of the material to an analyte gas component at the selected temperature for a period of at least about one minute.

55. A method according to claim 52 wherein the electrical response is selected from the group consisting of resistance, impedance, capacitance, voltage or current.

56. A method according to claim 52 wherein the array is situated within the gas mixture, which has a temperature of about 400° C. or more.

57. A method according to claim 52 wherein the array is situated in the gas mixture, which has a temperature of less than about 400° C., arid the array has a substantially constant temperature above 500° C.

58. A method according to claim 52 wherein the component gases in the gas mixture are not separated.

59. A method according to claim 52 wherein the analysis performed comprises calculating the concentration within the gas mixture of the individual gas component.

60. A method according to claim 52 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

61. A method according to claim 52 wherein the gas mixture comprises one or more members of the group consisting of oxygen, a nitrogen oxide, a hydrocarbon, and ammonia.

62. A method according to claim 52 wherein the gas mixture comprises one or more members of the group consisting of a nitrogen oxide and ammonia.

63. A method according to claim 52 wherein the gas mixture comprises one or more members of the group consisting of oxygen and a hydrocarbon.

64. A method according to claim 52 wherein the gas mixture is an emission from a combustion process.

65. A method according to claim 52 wherein the gas mixture is provided from a manufacturing process, a waste stream, environmental monitoring, or a medical, agricultural, food or beverage operation.

66. A method according to claim 52 wherein at least one chemo/electro-active material is a metal oxide.

67. A method according to claim 66 wherein the chemo/electro-active materials comprise one or more members of the group consisting of $M^1O_x$, $M^1_aM^2_bO_x$, and $M^1_aM^2_bM^3_cO_x$ wherein $M^1$, $M^2$ and $M^3$ are metals that form stable oxides when fired in the presence of oxygen above 500° C.;

$M^1$ is selected from Periodic Groups 2–15 and the lanthanide group;

$M^2$ and $M^3$ are independently selected from Periodic Groups 1–15 and the lanthanide group;

a, b, and c are each independently in the range of about 0.0005 to about 1, provided that a+b+c=1; and x is a number sufficient so that the oxygen present balances the charges of the other elements in the compound.

68. A method according to claim 66 wherein the chemo/electro-active materials comprise one or more members of the group consisting of $M^1O_x$, $M^1_aM^2_bO_x$, and $M^1_aM^2_bM^3_cO_x$ wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;

a, b, and c are each independently in the range of about 0.0005 to about 1, provided that a+b+c=1; and x is a number sufficient so that the oxygen present balances the charges of the other elements in the compound.

69. A method according to claim 66 erein the chemo/electro-active materials comprise one or more members of the group consisting of $M^1O_x$, $M^1_aM^2_bO_x$, and $M^1_aM^2_bM^3_cO_x$ wherein $M^1 O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;

$M^1_aM^2_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, or $Ta_aTi_bO_x$ with frit additive; and $M^1_aM^2_bM^3_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$;

a, b, arid c are each independently in the range of about 0.0005 to about 1, provided that a+b+c=1; and x is a number sufficient so that the oxygen present balances the charges of the other elements in the compound.

70. A method according to claim 66 wherein the chemo/electro-active materials comprise first and second chemo/electro-active materials selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$, (iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;

a, b and c are each independently about 0.0005 to about 1, provided that a+b+c=1; and x is a number sufficient so that the oxygen present balances the charges of the other elements in the compound.

71. A method for calculating the concentration of at least two individual analyte gas components in a multi-component gas mixture having a temperature of about 400° C. or more, comprising:

(a) providing within the gas mixture an array of at least three chemo/electro-active materials, each chemo/electro-active material having a different electrical response characteristic upon exposure to each of the individual analyte gas components than each of the other chemo/electro-active materials, wherein at least one chemo/electro-active material, when at a temperature of about 400° C. or more,
  (i) has an electrical resistivity in the range of about 1 ohm-cm to about $10^5$ ohm-cm, and
  (ii) exhibits a change in electrical resistance of at least about 0.1 percent upon exposure of the material to an analyte gas component, as compared to the resistance before exposure;
(b) heating the array to a temperature above 500° C.;
(c) determining an electrical response of each chemo/electro-active material upon exposure of the array to the unseparated components of the gas mixture;
(d) inputting only the electrical responses of the chemo/electro-active materials to a pattern recognition technique; and
(e) calculating the concentration of each of the individual analyte gas components from the inputs in step (d).

72. A method according to claim 71 wherein the electrical response characteristic of each material upon exposure to the gas mixture at a selected temperature is quantifiable as a value, and the response value of at least one material is constant or varies by no more than about twenty percent during exposure of the material to an analyte gas component at the selected temperature for a period of at least about one minute.

73. A method according to claim 71 wherein the electrical response is selected from the group consisting of resistance, impedance, capacitance, voltage or current.

74. A method according to claim 71 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

75. A method according to claim 71 wherein the gas mixture comprises one or more members of the group consisting of oxygen, a nitrogen oxide, a hydrocarbon, and ammonia.

76. A method according to claim 71 wherein the gas mixture comprises one or more members of the group consisting of a nitrogen oxide and ammonia.

77. A method according to claim 71 wherein the gas mixture comprises one or more members of the group consisting of oxygen and a hydrocarbon.

78. A method according to claim 71 wherein the gas mixture is an emission from a combustion process.

79. A method according to claim 71 wherein the gas mixture is provided from a manufacturing process, a waste stream, environmental monitoring, or a medical, agricultural, food or beverage operation.

80. A method according to claim 71 wherein at least one chemo/electro-active material is a metal oxide.

81. A method according to claim 80 wherein the chemo/electro-active materials comprise one or more members of the group consisting of $M^1O_x$, $M^1{}_aM^2{}_bO_x$, and $M^1{}_aM^2{}_bM^3{}_cO_x$ wherein $M^1$, $M^2$ and $M^3$ are metals that form stable oxides when fired in the presence of oxygen above 500° C.;
  $M^1$ is selected from Periodic Groups 2–15 and the lantharude group;
  $M^2$ and $M^3$ are independently selected from Periodic Groups 1–15 and the lanthanide group;
  a, b, and c are each independently in the range of about 0.0005 to about 1, provided that a+b+c=1; and
  x is a number sufficient so that the oxygen present balances the charges of the other elements in the compound.

82. A method according to claim 80 wherein the chemo/electro-active materials comprise one or more members of the group consisting of $M^1O_x$, $M^1{}_aM^2{}_bO_x$, and $M^1{}_aM^2{}_bM^3{}_cO_x$ wherein
  $M^1$ is selected from the group consisting of Ce, Co, Cu, Fe, Ga, Nb, Ni, Pr, Ru, Sn, Ti, Tm, W, Yb, Zn, and Zr;
  $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$;
  a, b, and c are each independently in the range of about 0.0005 to about 1, provided that a+b+c=1; and
  x is a number sufficient so that the oxygen present balances the charges of the other elements in the compound.

83. A method according to claim 80 wherein the chemo/electro-active materials comprise one or more members of the group consisting of $M^1O_x$, $M^1{}_aM^2{}_bO_x$, and $M^1{}_aM^2{}_bM^3{}_cO_x$ wherein
  $M^1O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;
  $M^1{}_aM^2{}_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZn_aO_x$, $Zn_aZr_bO_x$, $Al_aNi_bO_x$ with frit additive, $Cr_aTi_bO_x$ with frit additive, $Fe_aNi_bO_x$ With frit additive, $Fe_aTi_bO_x$ with frit additive, $Nb_aTi_bO_x$ with frit additive, $Nb_aW_bO_x$ With frit additive, $Ni_aZn_bO_x$ x with frit additive, $Ni_aZr_bO_x$ with frit additive, or $Ta_aTi_bO_x$ with frit additive; and
  $M^1{}_aM^2{}_bM^3{}_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$;

a, b, and c are each independently in the range of about 0.0005 to about 1, provided that a+b+c=1; and x is a number sufficient so that the oxygen present balances the charges of the other elements in the compound.

84. A method according to claim 80 wherein the chemo/electro-active materials comprise first and second chemo/electro-active materials selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;

a, b and c are each independently about 0.0005 to about 1, provided that a+b+c=1; and x is a number sufficient so that the oxygen present balances the charges of the other elements in the compound.

85. A method for analyzing at least one individual gas component in a multi-component gas mixture, comprising:

(a) providing an array of at least two chemo/electro-active materials, each chemo/electro-active material having a different electrical response characteristic upon exposure at a selected temperature to the individual gas component than each of the other chemo/electro-active materials, the electrical response characteristic of each material being quantifiable as a value, wherein the response value of at least one material is constant or varies by no more than about twenty percent during exposure of the material to an individual gas component at the selected temperature for a period of at least about one minute;

(b) heating the array to a temperature above 500° C.;

(c) determining the electrical response value of each chemo/electro-active material upon exposure of the array to the gas mixture;

(d) inputting only the electrical responses of the chemo/electro-active materials to a pattern recognition technique; and (e) performing an analysis of the individual gas component from the inputs in step (d).

86. A method according to claim 85 wherein at least one chemo/electro-active material, when at a temperature of about 400° C. or more, (i) has an electrical resistivity in the range of about 1 ohm-cm to about $10^5$ ohm-cm, and (ii) exhibits a change in electrical resistance of at least about 0.1 percent upon exposure of the material to an analyte gas component, as compared to the resistance before exposure.

87. A method according to claim 85 wherein the electrical response is selected from the group consisting of resistance, impedance, capacitance, voltage or current.

88. A method according to claim 85 wherein the array is situated within the gas mixture, which has a temperature of about 400° C. or more.

89. A method according to claim 85 wherein the array is situated in the gas mixture, which has a temperature of less than about 400° C., and the array has a substantially constant temperature above 500° C.

90. A method according to claim 85 wherein the component gases in the mixture are not separated.

91. A method according to claim 85 wherein the analysis performed comprises calculating the concentration within the gas mixture of the individual gas component.

92. A method according to claim 85 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

93. A method according to claim 85 wherein the gas mixture comprises one or more members of the group consisting of oxygen, a nitrogen oxide, a hydrocarbon, and ammonia.

94. A method according to claim 85 in the gas mixture comprises one or more members of the group consisting of a nitrogen oxide and ammonia.

95. A method according to claim 85 wherein the gas mixture comprises one or more members of the group consisting of oxygen and a hydrocarbon.

96. A method according to claim 85 wherein the gas mixture is an emission from a combustion process.

97. A method according to claim 85 wherein the gas mixture is provided from a manufacturing process, a waste stream, environmental monitoring, or a medical, agricultural, food or beverage operation.

98. A method according to claim 85 wherein at least one chemo/electro-active material is a metal oxide.

99. A method according to claim 98 wherein the chemo/electro-active materials comprise one or more members of the group consisting of $M^1O_x$, $M^1_aM^2_bO_x$, and $M^1_aM^2_bM^3_cO_x$ wherein $M^1$, $M^2$ and $M^3$ are metals that form stable oxides when fired in the presence of oxygen above 500° C.;

$M^1$ is selected from Periodic Groups 2–15 and the lanthanide group;

$M^2$ and $M^3$ are independently selected from Periodic Groups 1–15 and the lanthanide group;

a, b, and c are each independently in the range of about 0.0005 to about 1, provided that a+b+c=1; and x is a number sufficient so that the oxygen present balances the charges of the other elements in the compound.

100. A method according to claim 98 wherein the chemo/electro-active materials comprise one or more members of the group consisting of $M^1O_x$, $M^1_aM^2_bO_x$, and $M^1_aM^2_bM^3_cO_x$ wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;

a, b, and c are each independently in the range of about 0.0005 to about 1, provided that a+b+c=1; and x is a number sufficient so that the oxygen present balances the charges of the other elements in the compound.

101. A method according to claim 98 wherein the chemo/electro-active materials comprise one or more members of the group consisting of $M^1_{Ox}$, $M^1_aM^2_bO_x$, and $M^1_aM^2_bM^3_cO_x$ wherein $M^1O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;

$M^1_aM^2_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_bSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZn_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, or $Ta_aTi_bO_x$ with frit additive; and $M^1_aM^2_bM^3_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_aTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$;

a, b, and c are each independently in the range of about 0.0005 to about 1, provided that a+b+c=1; and x is a number sufficient so that the oxygen present balances the charges of the other elements in the compound.

102. A method according to claim 98 wherein the chemo/electro-active materials comprise first and second chemo/electro-active materials selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$, a, b and c are each independently about 0.0005 to about 1, provided that a+b+c=1; and x is a number sufficient so that the oxygen present balances the charges of the other elements in the compound.

* * * * *